US011660082B2

(12) United States Patent
Heiman

(10) Patent No.: US 11,660,082 B2
(45) Date of Patent: May 30, 2023

(54) DILATION SYSTEM

(71) Applicant: DePuy Synthes Products, Inc., Raynham, MA (US)

(72) Inventor: Stephen Heiman, Exton, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 374 days.

(21) Appl. No.: 16/785,207

(22) Filed: Feb. 7, 2020

(65) Prior Publication Data

US 2020/0170632 A1 Jun. 4, 2020

Related U.S. Application Data

(63) Continuation of application No. 16/050,820, filed on Jul. 31, 2018, now Pat. No. 10,582,917, which is a (Continued)

(51) Int. Cl.
*A61B 17/02* (2006.01)
*A61B 5/24* (2021.01)
(Continued)

(52) U.S. Cl.
CPC ............ *A61B 17/0218* (2013.01); *A61B 5/24* (2021.01); *A61B 17/025* (2013.01); *A61B 17/3462* (2013.01); *A61B 17/3439* (2013.01); *A61B 17/3468* (2013.01); *A61B 2017/00022* (2013.01); *A61B 2017/0256* (2013.01); *A61B 2017/0262* (2013.01)

(58) Field of Classification Search
CPC ... A61B 17/02; A61B 17/0218; A61B 17/025; A61B 2017/0256; A61B 2017/0262; A61B 17/3439; A61B 17/3462; A61B 17/3468; A61B 29/00
See application file for complete search history.

(56) References Cited

U.S. PATENT DOCUMENTS 3,486,505 A 12/1969 Morrison
4,350,151 A 9/1982 Scott
(Continued)

FOREIGN PATENT DOCUMENTS

CN 102727309 A 10/2012
DE 9415039 U1 11/1994
(Continued)

OTHER PUBLICATIONS

International Search Report and Written Opinion (PCT/US2012/063061); dated Aug. 6, 2013.
(Continued)

*Primary Examiner* — Larry E Waggle, Jr.
(74) *Attorney, Agent, or Firm* — Dunlap Codding, P.C.

(57) ABSTRACT

A dilation system for accessing a surgical target site to perform surgical procedures. In one version, the dilation system includes a wedge assembly and an actuating mechanism. The wedge assembly comprises includes a base and a plurality of blades extending from the base so that the distal end of the blades extend away from the base. The mechanism is operably associated with the blades so as to cause the distal end of the blades to move from a closed condition to an expanded condition.

9 Claims, 28 Drawing Sheets

Related U.S. Application Data continuation of application No. 14/046,685, filed on Oct. 4, 2013, now Pat. No. 10,039,540, which is a continuation-in-part of application No. PCT/US2012/063061, filed on Nov. 1, 2012.

(60) Provisional application No. 61/554,397, filed on Nov. 1, 2011.

(51) Int. Cl.
    *A61B 17/34*     (2006.01)
    *A61B 17/00*     (2006.01)

(56) References Cited

U.S. PATENT DOCUMENTS

| | | |
|---|---|---|
| 4,573,448 A | 3/1986 | Kambin |
| 4,646,738 A | 3/1987 | Trott |
| 4,678,459 A | 7/1987 | Onik et al. |
| 4,716,901 A | 1/1988 | Jackson et al. |
| 4,863,430 A | 9/1989 | Klyce et al. |
| 4,888,146 A | 12/1989 | Dandeneau |
| 5,080,662 A | 1/1992 | Paul |
| 5,195,541 A | 3/1993 | Obenchain |
| 5,275,611 A | 1/1994 | Behl |
| 5,285,795 A | 2/1994 | Ryan et al. |
| 5,395,317 A | 3/1995 | Kambin |
| 5,439,464 A | 8/1995 | Shapiro |
| 5,503,617 A | 4/1996 | Jako |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,662,300 A | 9/1997 | Michelson |
| 5,688,222 A | 11/1997 | Hluchy et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,779,629 A | 7/1998 | Hohlen |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey Jr et al. |
| 5,910,155 A | 6/1999 | Ratcliff et al. |
| 5,954,635 A | 9/1999 | Foley et al. |
| 5,964,698 A | 10/1999 | Fowler |
| 6,033,105 A | 3/2000 | Barker et al. |
| 6,053,907 A | 4/2000 | Zirps |
| 6,063,021 A | 5/2000 | Hossain et al. |
| 6,110,182 A | 8/2000 | Mowlai-Ashtiani |
| 6,200,322 B1 | 3/2001 | Branch et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,558,407 B1 | 5/2003 | Ivando et al. |
| 6,575,899 B1 | 6/2003 | Foley et al. |
| 6,579,281 B2 | 6/2003 | Palmer et al. |
| 6,626,830 B1 | 9/2003 | Califiore et al. |
| 6,648,915 B2 | 11/2003 | Sazy |
| 6,676,597 B2 | 1/2004 | Guenst et al. |
| 6,688,564 B2 | 2/2004 | Salvermoser et al. |
| 6,689,096 B1 | 2/2004 | Loubens et al. |
| 6,709,389 B2 | 3/2004 | Farascioni |
| 6,755,841 B2 | 6/2004 | Fraser et al. |
| 6,758,809 B2 | 7/2004 | Briscoe et al. |
| 6,808,505 B2 | 10/2004 | Kadan |
| 6,887,198 B2 | 5/2005 | Phillips et al. |
| 6,932,765 B2 | 8/2005 | Berg |
| 6,983,930 B1 | 1/2006 | La Mendola et al. |
| 7,087,058 B2 | 8/2006 | Cragg |
| 7,104,986 B2 | 9/2006 | Hovda et al. |
| 7,108,698 B2 | 9/2006 | Robbins et al. |
| 7,137,949 B2 | 11/2006 | Scirica et al. |
| 7,182,731 B2 | 2/2007 | Nguyen et al. |
| 7,226,413 B2 | 6/2007 | McKinley |
| 7,341,556 B2 | 3/2008 | Shalman |
| 7,434,325 B2 | 10/2008 | Foley et al. |
| 7,435,219 B2 | 10/2008 | Kim |
| 7,481,766 B2 | 1/2009 | Lee et al. |
| 7,494,463 B2 | 2/2009 | Nehls |
| 7,582,058 B1 | 9/2009 | Miles et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,691,057 B2 | 4/2010 | Miles et al. |
| 7,722,622 B2 | 5/2010 | Evans et al. |
| 7,771,384 B2 | 8/2010 | Ravo |
| 7,785,253 B1 | 8/2010 | Arambula et al. |
| 7,794,456 B2 | 9/2010 | Sharps et al. |
| 7,811,303 B2 | 10/2010 | Fallin et al. |
| 7,931,579 B2 | 4/2011 | Bertolero et al. |
| 7,935,051 B2 | 5/2011 | Miles et al. |
| 7,946,981 B1 | 5/2011 | Cubb |
| 7,951,141 B2 | 5/2011 | Sharps et al. |
| 7,959,564 B2 | 6/2011 | Ritland |
| RE42,525 E | 7/2011 | Simonson |
| 7,988,623 B2 | 8/2011 | Pagliuca et al. |
| 8,005,535 B2 | 8/2011 | Gharib et al. |
| 8,007,492 B2 | 8/2011 | DiPoto et al. |
| 8,027,716 B2 | 9/2011 | Gharib et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,092,464 B2 | 1/2012 | McKay |
| 8,096,944 B2 | 1/2012 | Harrel |
| 8,114,019 B2 | 2/2012 | Miles et al. |
| 8,202,216 B2 | 6/2012 | Melkent et al. |
| 8,236,006 B2 | 8/2012 | Hamada |
| 8,262,571 B2 | 9/2012 | Ritland |
| 8,313,430 B1 | 11/2012 | Pimenta |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,617,062 B2 | 12/2013 | Mire et al. |
| 8,622,894 B2 | 1/2014 | Banik et al. |
| 8,636,655 B1 | 1/2014 | Childs |
| 8,690,764 B2 | 4/2014 | Clark et al. |
| 8,702,600 B2 | 4/2014 | Perrow |
| 8,721,536 B2 | 5/2014 | Marino et al. |
| 8,740,779 B2 | 6/2014 | Yoshida |
| 8,784,421 B2 | 7/2014 | Carrison et al. |
| 8,795,167 B2 | 8/2014 | Ainsworth et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,876,904 B2 | 11/2014 | Primenta et al. |
| 8,894,573 B2 | 11/2014 | Loftus et al. |
| 8,894,653 B2 | 11/2014 | Solsberg et al. |

(56) References Cited

U.S. PATENT DOCUMENTS

| | | |
|---|---|---|
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,605 B2 | 1/2015 | Greenberg |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,131,948 B2 | 9/2015 | Fang et al. |
| 9,144,374 B2 | 9/2015 | Maurice, Jr. |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,232,935 B2 | 1/2016 | Brand et al. |
| 9,247,997 B2 | 2/2016 | Stefanchik et al. |
| 9,265,490 B2 | 2/2016 | Bowman et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,009 B2 | 7/2016 | Fatone et al. |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 9,888,911 B2 | 2/2018 | Siegal |
| 2002/0022762 A1 | 2/2002 | Beane et al. |
| 2002/0116006 A1 | 8/2002 | Cohen |
| 2002/0138020 A1 | 9/2002 | Pflueger |
| 2003/0083555 A1 | 5/2003 | Hunt et al. |
| 2003/0083688 A1 | 5/2003 | Simonson |
| 2003/0171744 A1 | 9/2003 | Leung et al. |
| 2003/0191474 A1 | 10/2003 | Cragg et al. |
| 2003/0195405 A1 | 10/2003 | Marino et al. |
| 2004/0064147 A1 | 4/2004 | Struble |
| 2004/0122446 A1 | 6/2004 | Solar |
| 2004/0127992 A1 | 7/2004 | Serhan et al. |
| 2004/0143165 A1 | 7/2004 | Alleyne |
| 2004/0225196 A1 | 11/2004 | Ruane |
| 2005/0085692 A1 | 4/2005 | Kiehn et al. |
| 2005/0090848 A1 | 4/2005 | Adams |
| 2005/0137461 A1 | 6/2005 | Marchek et al. |
| 2005/0149035 A1 | 7/2005 | Pimenta et al. |
| 2005/0165408 A1 | 7/2005 | Puno et al. |
| 2005/0187570 A1 | 8/2005 | Nguyen et al. |
| 2005/0234304 A1 | 10/2005 | Dewey et al. |
| 2005/0256525 A1 | 11/2005 | Culbert et al. |
| 2006/0106416 A1 | 5/2006 | Raymond et al. |
| 2006/0195017 A1 | 8/2006 | Schluzas et al. |
| 2006/0206008 A1 | 9/2006 | Dalton |
| 2006/0206118 A1 | 9/2006 | Kim et al. |
| 2006/0217754 A1 | 9/2006 | Boehm et al. |
| 2007/0038216 A1 | 2/2007 | Hamada |
| 2007/0055259 A1 | 3/2007 | Norton et al. |
| 2007/0073110 A1 | 3/2007 | Larson et al. |
| 2007/0073111 A1 | 3/2007 | Bass |
| 2007/0100212 A1 | 5/2007 | Pimenta et al. |
| 2007/0123753 A1 | 5/2007 | Abdelgany |
| 2007/0129634 A1 | 6/2007 | Hickey et al. |
| 2007/0149975 A1 | 6/2007 | Oliver et al. |
| 2007/0156024 A1 | 7/2007 | Frasier et al. |
| 2007/0198062 A1 | 8/2007 | Miles et al. |
| 2007/0203396 A1 | 8/2007 | McCutcheon et al. |
| 2007/0185375 A1 | 9/2007 | Stad et al. |
| 2007/0208366 A1 | 9/2007 | Pellegrino et al. |
| 2007/0225556 A1 | 9/2007 | Ortiz et al. |
| 2007/0238932 A1 | 10/2007 | Jones et al. |
| 2007/0260113 A1 | 11/2007 | Otawara |
| 2007/0270875 A1 | 11/2007 | Bacher et al. |
| 2007/0282171 A1 | 12/2007 | Karpowicz et al. |
| 2008/0003325 A1 | 1/2008 | Seaver |
| 2008/0015621 A1 | 1/2008 | Emanuel |
| 2008/0021284 A1 | 1/2008 | Hestad et al. |
| 2008/0033251 A1 | 2/2008 | Araghi |
| 2008/0058606 A1 | 3/2008 | Miles et al. |
| 2008/0081951 A1 | 4/2008 | Frasier et al. |
| 2008/0188714 A1 | 8/2008 | McCaffrey |
| 2008/0215081 A1 | 9/2008 | Hsueh et al. |
| 2008/0262318 A1 | 10/2008 | Gorek et al. |
| 2008/0319290 A1 | 12/2008 | Mao et al. |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0069634 A1 | 3/2009 | Larkin |
| 2009/0105543 A1 | 4/2009 | Miller et al. |
| 2009/0124860 A1 | 5/2009 | Miles et al. |
| 2009/0156898 A1 | 6/2009 | Ichimura |
| 2009/0156902 A1 | 6/2009 | Dewey et al. |
| 2009/0187080 A1 | 7/2009 | Seex |
| 2009/0227845 A1 | 9/2009 | Lo et al. |
| 2009/0240111 A1 | 9/2009 | Kessler et al. |
| 2009/0259107 A1 | 10/2009 | Crenshaw et al. |
| 2009/0275802 A1 | 11/2009 | Hawkes et al. |
| 2009/0275804 A1 | 11/2009 | Bertagnoli |
| 2009/0287061 A1 | 11/2009 | Feigenbaum et al. |
| 2009/0306586 A1 | 12/2009 | Ross et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0022845 A1 | 1/2010 | Ott et al. |
| 2010/0076476 A1 | 3/2010 | To et al. |
| 2010/0076502 A1 | 3/2010 | Guyer et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0217088 A1* | 8/2010 | Heiges .................. A61B 1/32 600/206 |
| 2010/0222644 A1 | 9/2010 | Sebastian et al. |
| 2010/0256446 A1 | 10/2010 | Raju |
| 2010/0274275 A1 | 10/2010 | Stammberger et al. |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2010/0317989 A1 | 12/2010 | Gharib et al. |
| 2011/0028791 A1 | 2/2011 | Marino et al. |
| 2011/0034779 A1 | 2/2011 | Louftus et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0144439 A1 | 6/2011 | Miles et al. |
| 2011/0208226 A1 | 8/2011 | Fatone et al. |
| 2011/0230782 A1 | 9/2011 | Bartol et al. |
| 2011/0237898 A1 | 9/2011 | Stone et al. |
| 2011/0257487 A1 | 10/2011 | Thalgott et al. |
| 2011/0295070 A1 | 12/2011 | Yasunaga |
| 2011/0319941 A1 | 12/2011 | Bar et al. |
| 2012/0010471 A1 | 1/2012 | Mire et al. |
| 2012/0022575 A1 | 1/2012 | Mire et al. |
| 2012/0046527 A1 | 2/2012 | Cianfrani et al. |
| 2012/0095296 A1 | 4/2012 | Trieu et al. |

(56) References Cited

U.S. PATENT DOCUMENTS

| | | |
|---|---|---|
| 2012/0101338 A1 | 4/2012 | O'Prey et al. |
| 2012/0209273 A1 | 8/2012 | Zaretzka et al. |
| 2012/0221007 A1 | 8/2012 | Batten et al. |
| 2012/0232349 A1 | 9/2012 | Perrow |
| 2012/0232350 A1 | 9/2012 | Seex |
| 2012/0232552 A1 | 9/2012 | Morgenstern Lopez et al. |
| 2012/0245431 A1 | 9/2012 | Baudouin et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0261401 A1 | 10/2013 | Hawkins et al. |
| 2013/0274557 A1 | 10/2013 | Bowman et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0039264 A1 | 2/2014 | Heiman |
| 2014/0066940 A1 | 3/2014 | Fang et al. |
| 2014/0074170 A1 | 3/2014 | Mertens et al. |
| 2014/0088367 A1 | 3/2014 | DiMauro et al. |
| 2014/0128682 A1 | 5/2014 | Loebl et al. |
| 2014/0128979 A1 | 5/2014 | Womble |
| 2014/0135584 A1 | 5/2014 | Lee et al. |
| 2014/0142584 A1 | 5/2014 | Sweeney |
| 2014/0148647 A1 | 5/2014 | Okazaki |
| 2014/0172002 A1 | 6/2014 | Predick |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257035 A1 | 9/2014 | Blain |
| 2014/0257489 A1 | 9/2014 | Warren et al. |
| 2014/0275799 A1 | 9/2014 | Schuele |
| 2014/0275800 A1 | 9/2014 | Miles et al. |
| 2014/0276840 A1 | 9/2014 | Richter et al. |
| 2014/0277204 A1 | 9/2014 | Sandhu |
| 2014/0303666 A1 | 10/2014 | Heiman et al. |
| 2014/0316209 A1 | 10/2014 | Overes et al. |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0051448 A1 | 2/2015 | Hunt et al. |
| 2015/0065795 A1 | 3/2015 | Titus |
| 2015/0066039 A1 | 3/2015 | Siegal et al. |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2018/0271513 A1 | 9/2018 | Perrow et al. |

FOREIGN PATENT DOCUMENTS

| | | | |
|---|---|---|---|
| DE | 29916026 U1 | 12/1999 | |
| EP | 0537116 A1 | 4/1993 | |
| EP | 0792620 A2 | 9/1997 | |
| EP | 0807415 A2 | 11/1997 | |
| EP | 2179695 A2 | 4/2010 | |
| GB | 2481727 B | 1/2012 | |
| JP | 2003169809 | 6/2003 | |
| JP | 2003169809 A | 6/2003 | |
| WO | 1996/029014 | 9/1996 | |
| WO | 2001/056490 | 8/2001 | |
| WO | 2001/089371 | 11/2001 | |
| WO | 2002/002016 | 1/2002 | |
| WO | 2004/091426 | 10/2004 | |
| WO | 2004/103430 | 12/2004 | |
| WO | 2005/094695 | 10/2005 | |
| WO | 2005/096735 | 10/2005 | |
| WO | 2006/058079 | 6/2006 | |
| WO | 2007/016368 | 2/2007 | |
| WO | 2007/087536 | 8/2007 | |
| WO | 2008/121162 | 10/2008 | |
| WO | 2009/033207 | 3/2009 | |
| WO | 2009/046414 | 4/2009 | |
| WO | WO-2009046414 A1 * | 4/2009 | ......... A61B 17/0218 |
| WO | 2011/069036 | 6/2011 | |
| WO | 2011/097639 | 8/2011 | |
| WO | 2011/112878 | 9/2011 | |
| WO | 2011/130532 | 10/2011 | |
| WO | 2013/033426 | 3/2013 | |
| WO | 2013/059640 | 4/2013 | |
| WO | 2014/050236 | 4/2014 | |
| WO | 2014/100761 | 6/2014 | |
| WO | 2014/185334 | 11/2014 | |
| WO | 2016/111373 | 7/2016 | |
| WO | 2016/131077 | 8/2016 | |
| WO | 2016/168673 | 10/2016 | |
| WO | 2017/006684 | 1/2017 | |
| WO | 2017/015480 | 1/2017 | |
| WO | 2017/083648 | 5/2017 | |

OTHER PUBLICATIONS

Extended European Search Report (EP13163266.3); dated Oct. 30, 2013.
Partial European Search Report (EP13163266.3-1654); dated Jul. 12, 2013; 8 pages.
Extended European Search Report (EP13163266.3-1654); dated Oct. 30, 2013; 13 pages.
Percutaneous Transforaminal Endoscopic Disectomy: The Thessys Method; Menno Iprenburg; 17 pgs; 2008.
International Search Report and Written Opinion (PCT/US2015/043554); dated Nov. 19, 2015: 8 pgs.
International Search Report and Written Opinion (PCT/US2015/048485); dated Feb. 9, 2016; 16 pgs.
Invitation to Pay Fees (PCT/US2016/050022); dated Nov. 3, 2016; 2 pgs.
International Search Report and Written Opinion (PCT/US2015/060978) dated Feb. 15, 2016; 8 pgs.
International Search Report and Written Opinion (PCT/US2016/050022) dated Feb. 1, 2017; 19 pgs.
A hands-free region-of-interest selection interface for solo surgery with a wide-angle endoscope: preclinical proof of concept; Kyunghwa Jung Published online Aug. 8, 2016; 7 pgs.
Maxcess XLIF Surgical Technique; Oct. 16, 2012; 30 pgs.
Mechanomyography is more sensitive than EMG in detecting age-related sarcopenia; Journal of Biomechanics; vol. 43, Issue 3; Feb. 10, 2010 pp. 551-556; 20 pgs.

(56) References Cited

OTHER PUBLICATIONS

Iprenburg, M, "Percutaneous Transforaminal Endoscopic Discectomy: The Thessys Method," in Lewandrowski, K., et al., Minimally Invasive Spinal Fusion Techniques, Summit Communications, 2008 pp. 65-81.

\* cited by examiner

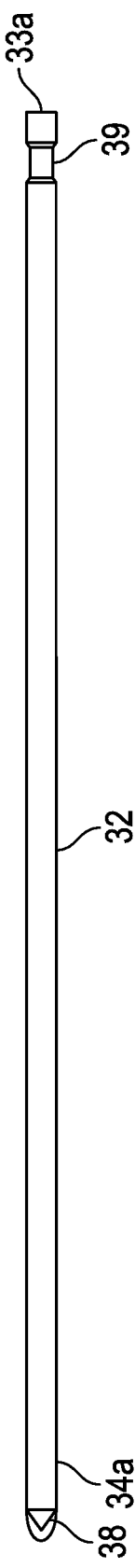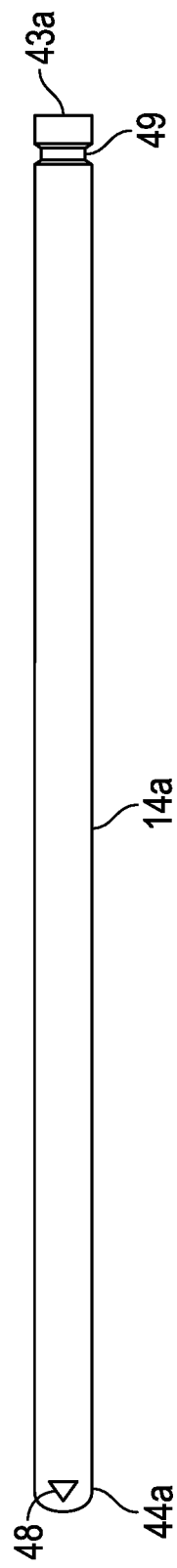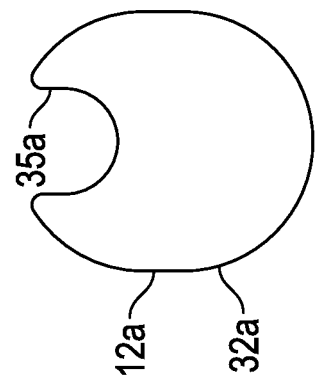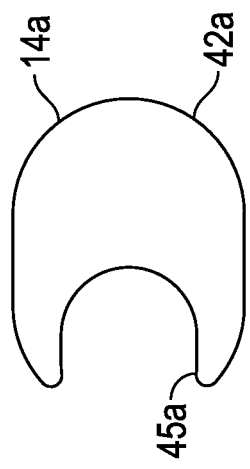

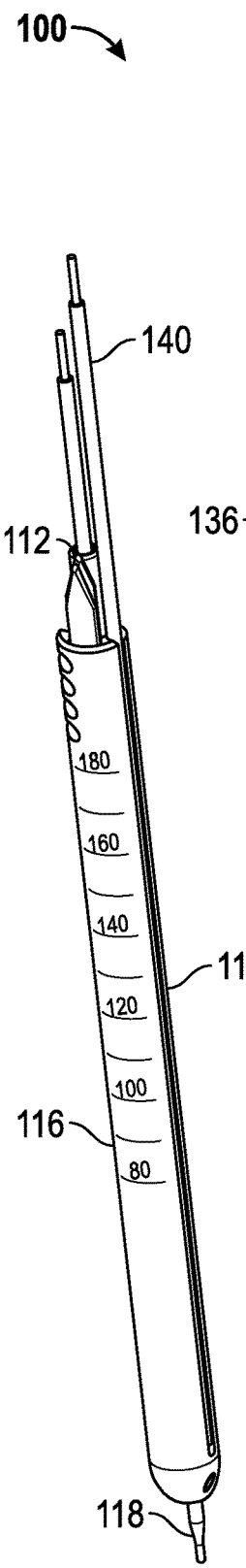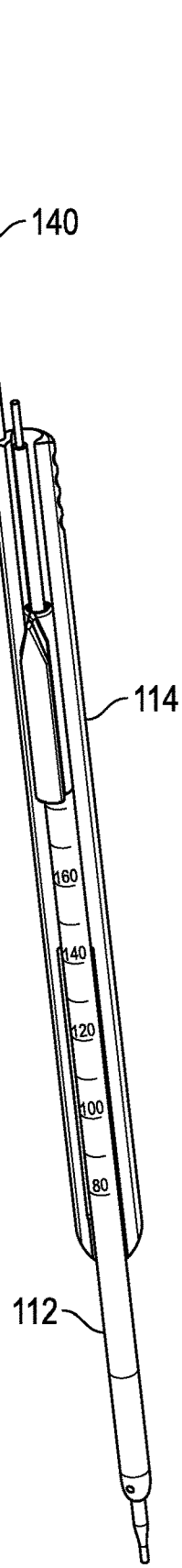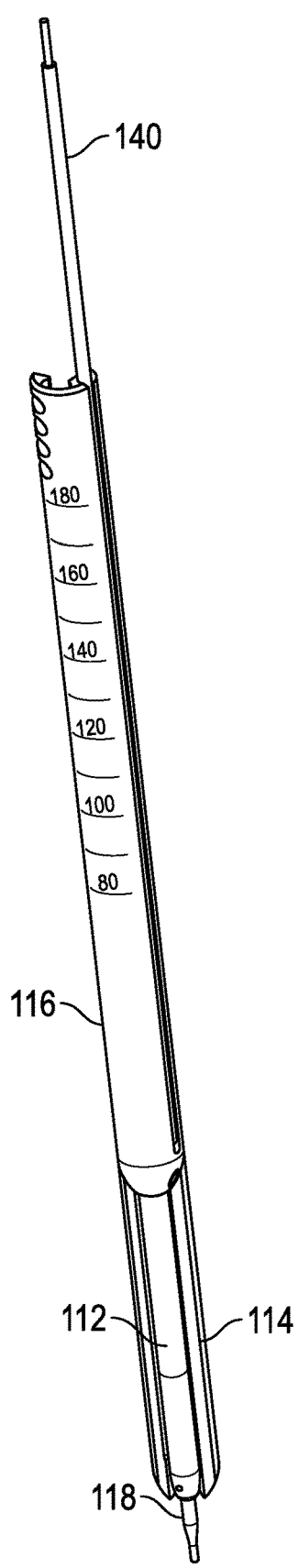
FIG. 14  FIG. 15A  FIG. 15B  FIG. 15C

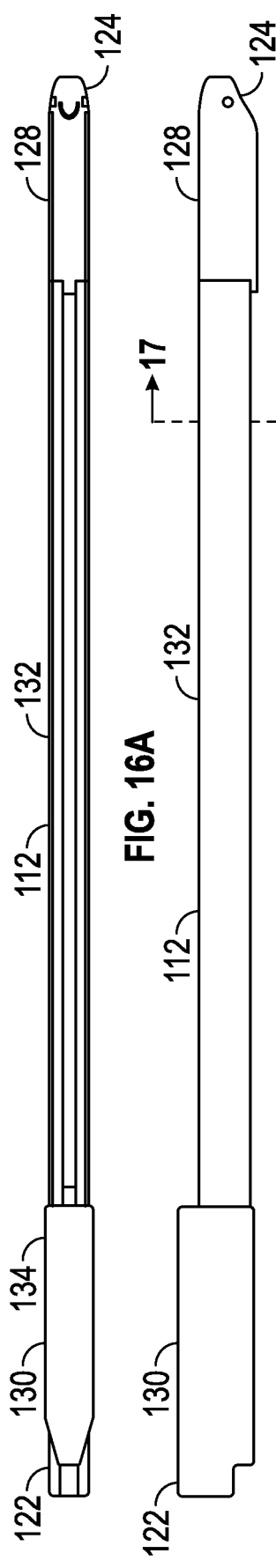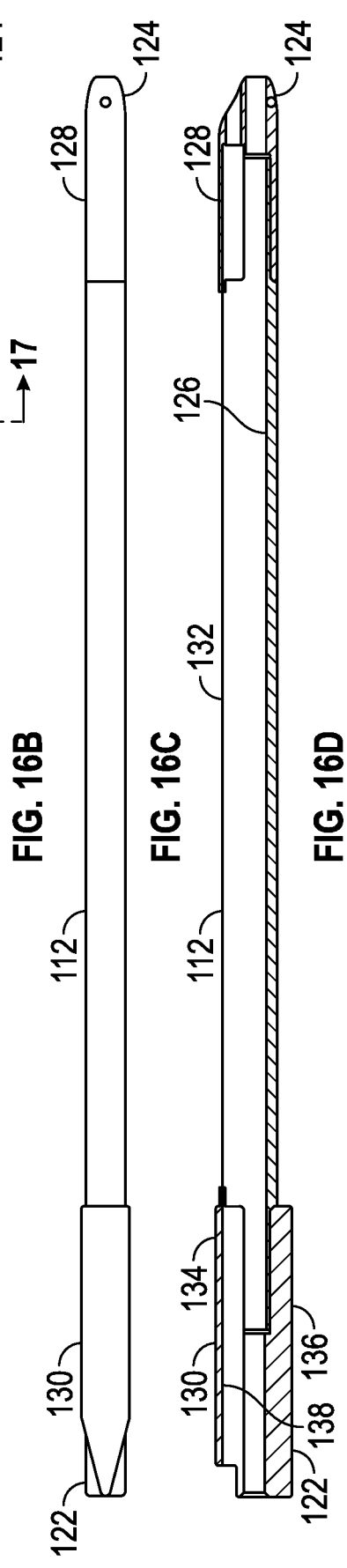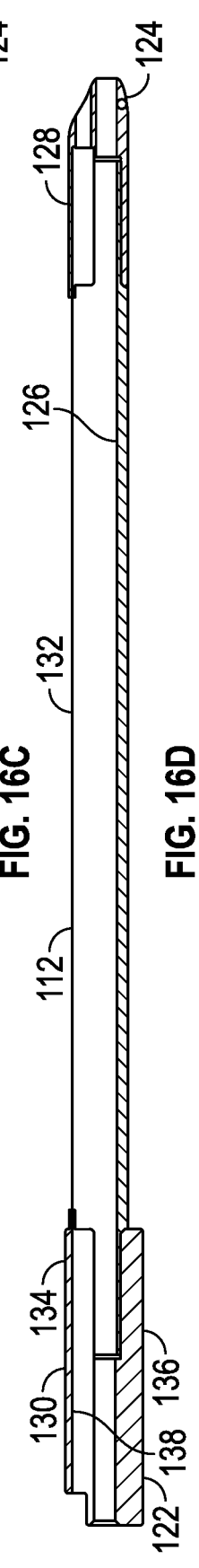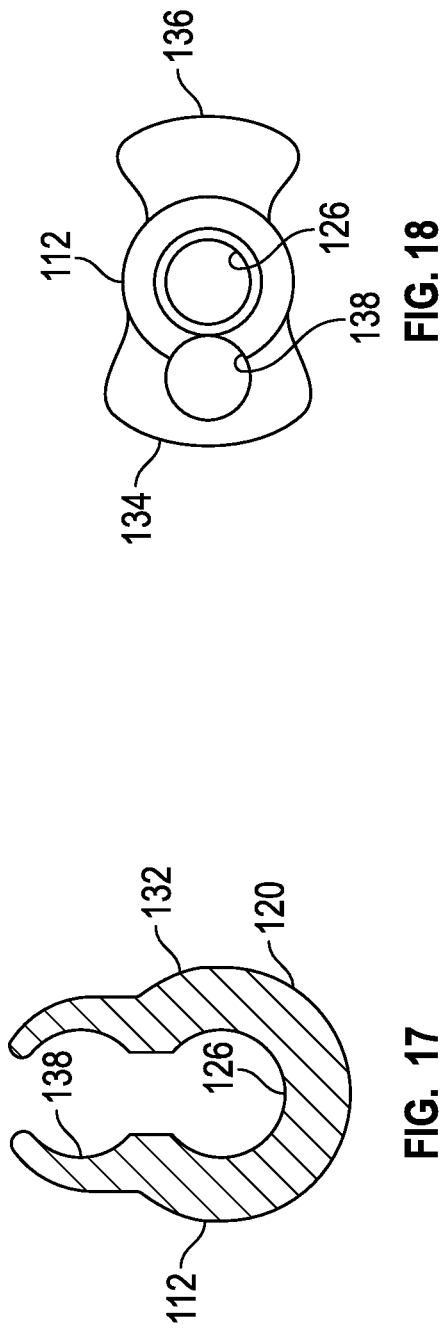

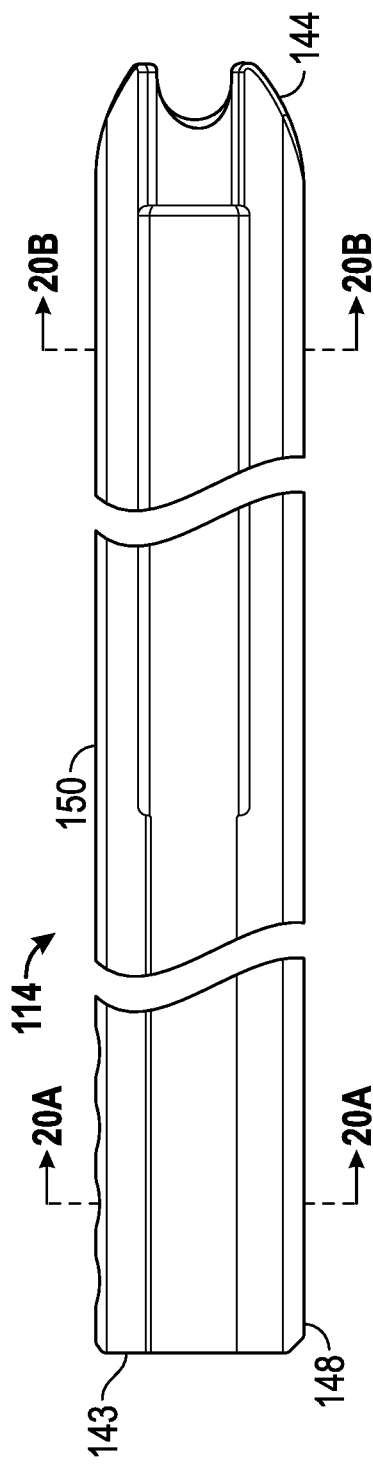
FIG. 19
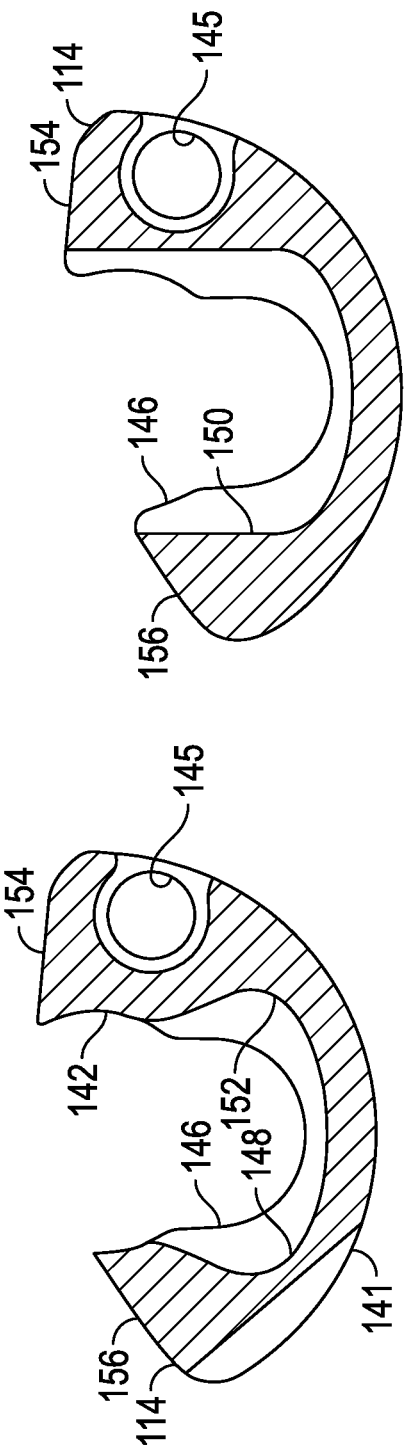
FIG. 20A
FIG. 20B

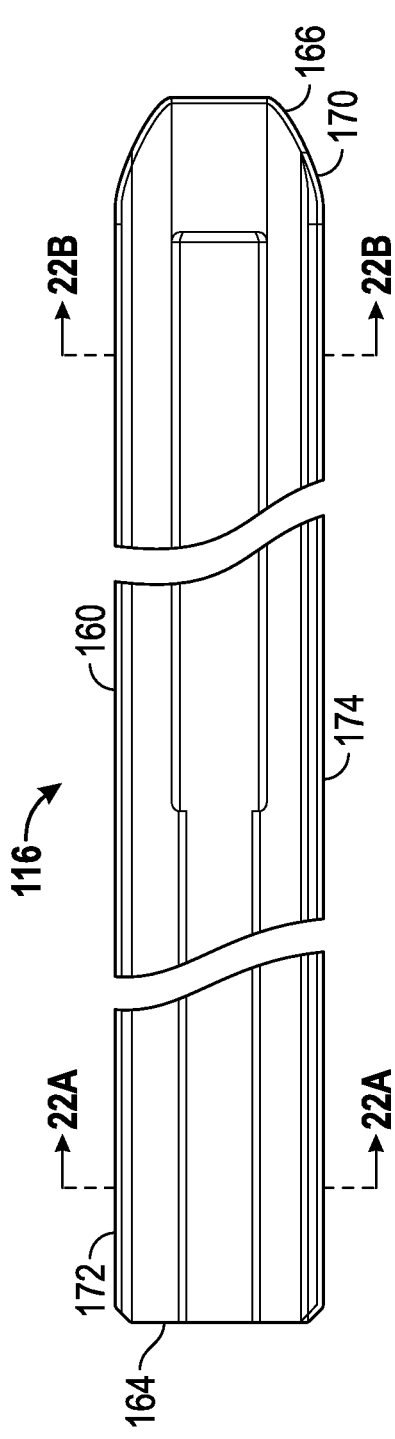
FIG. 21
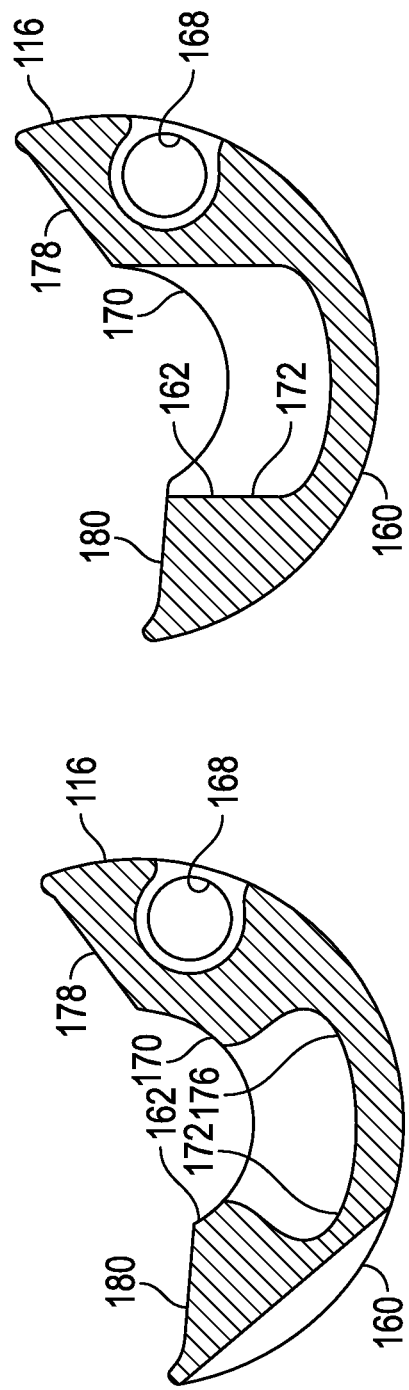
FIG. 22B
FIG. 22A

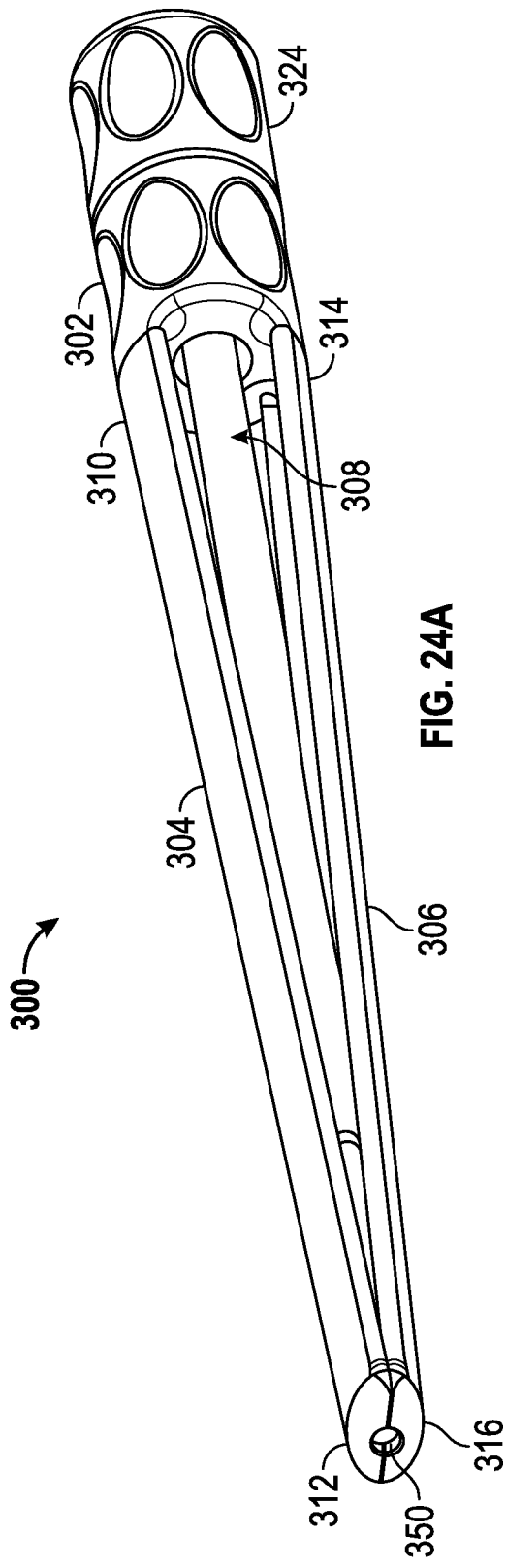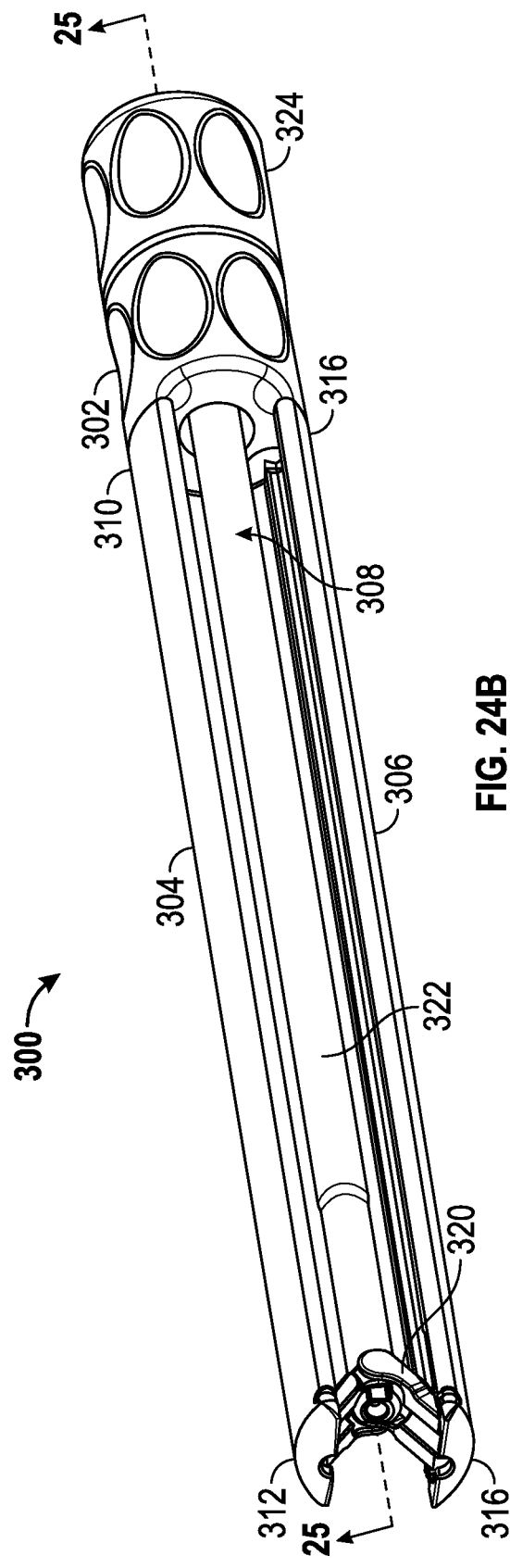
FIG. 24A
FIG. 24B

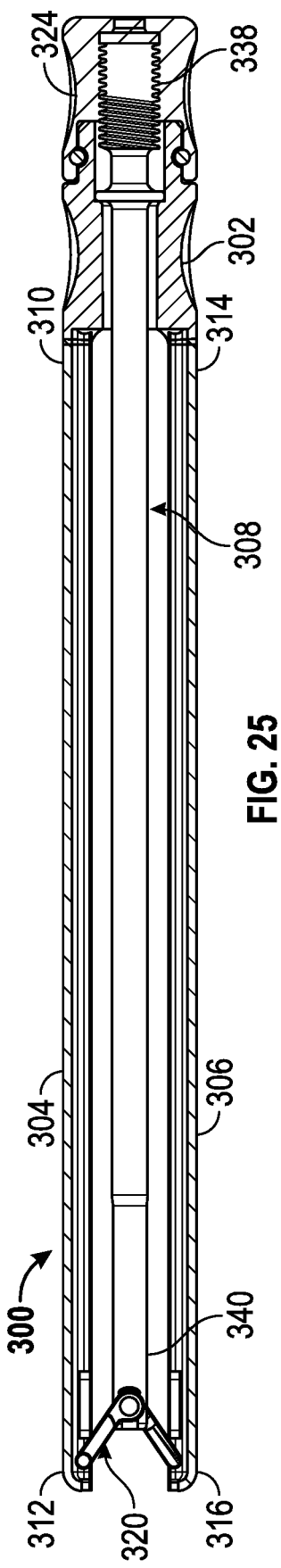
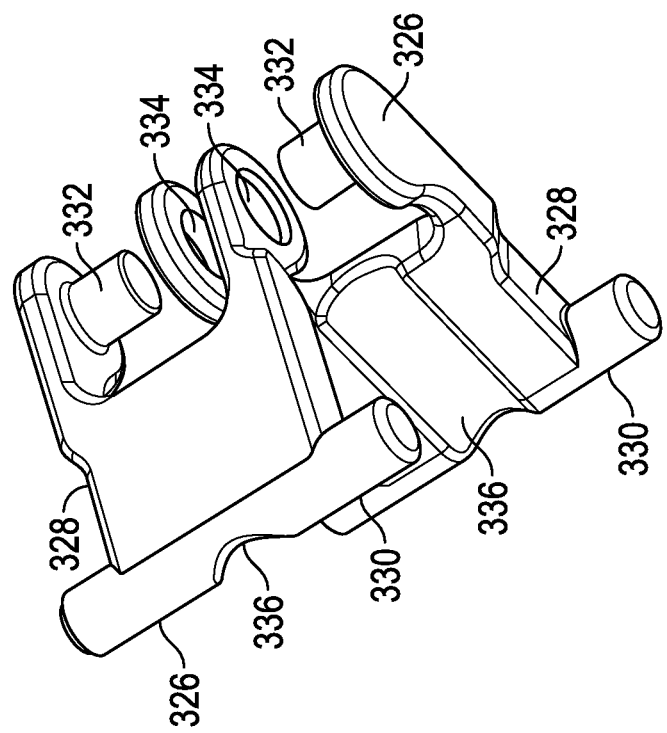
FIG. 25
FIG. 26

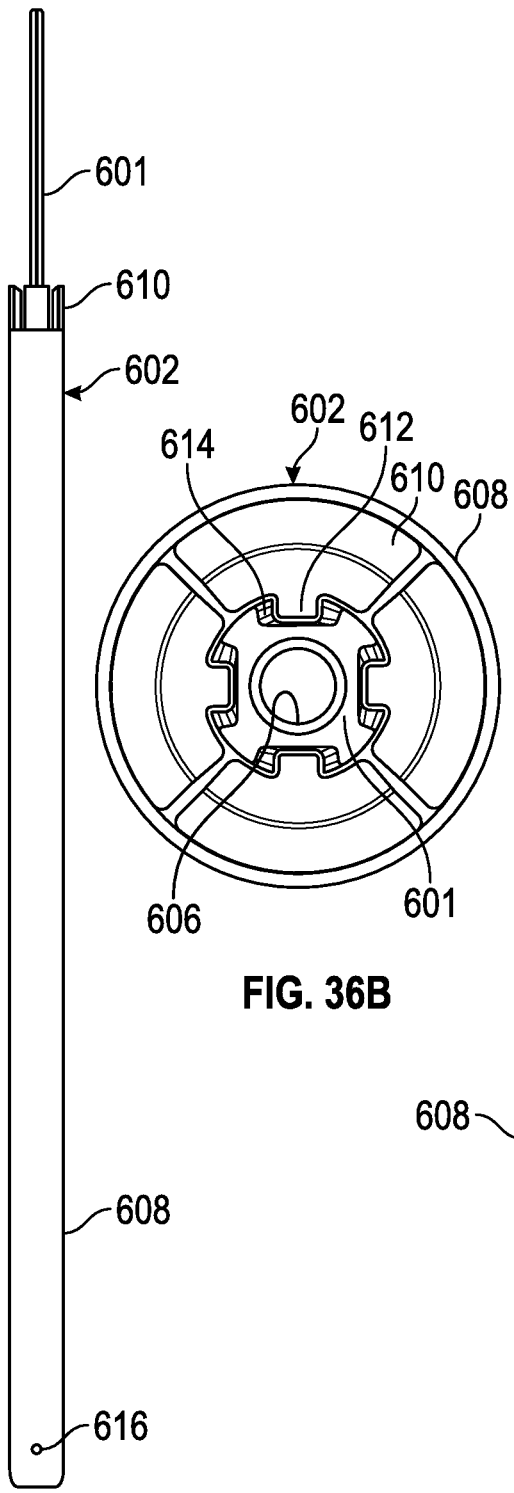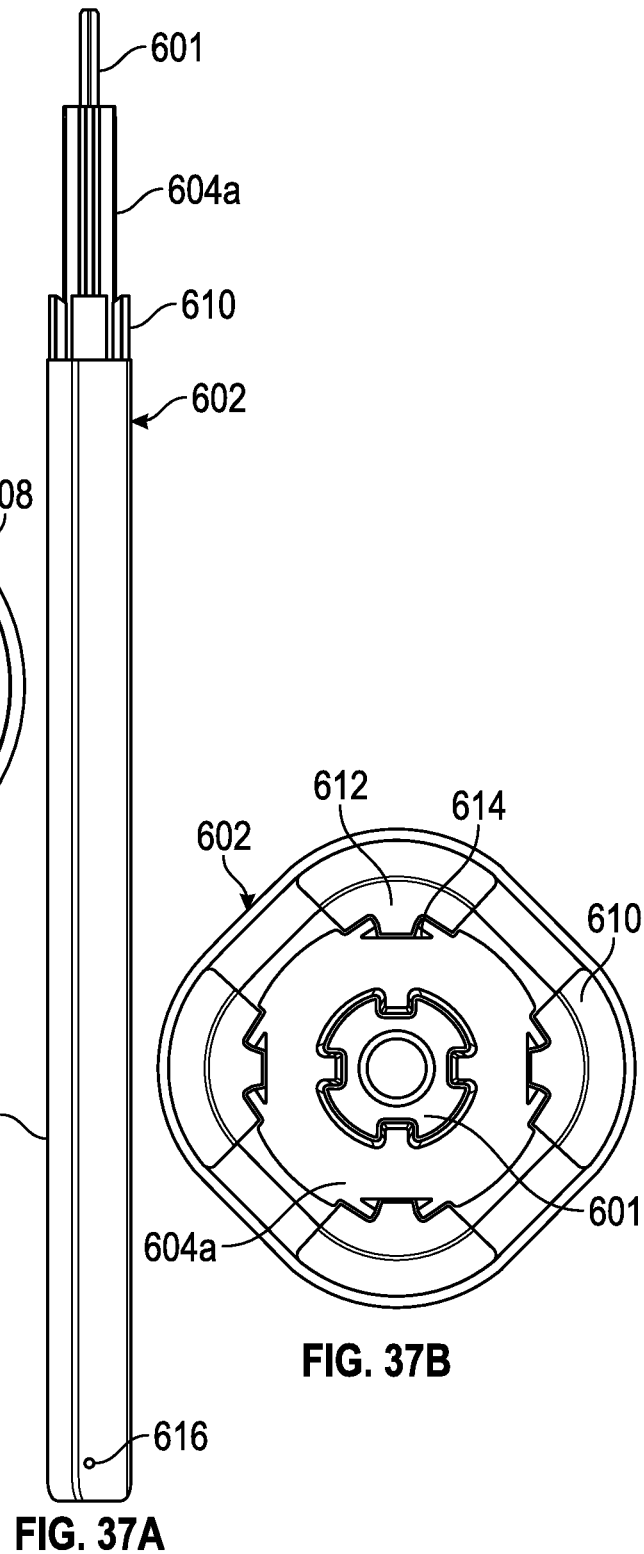
FIG. 36B
FIG. 36A
FIG. 37B
FIG. 37A

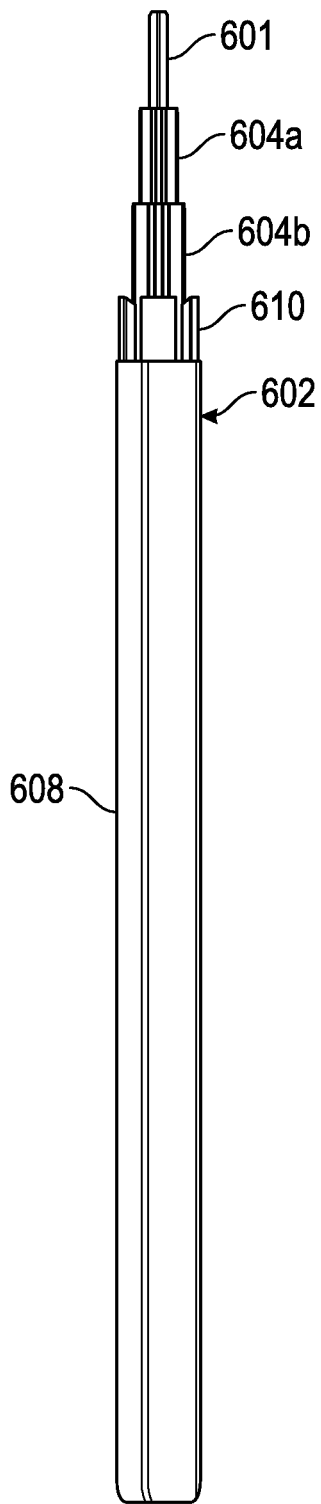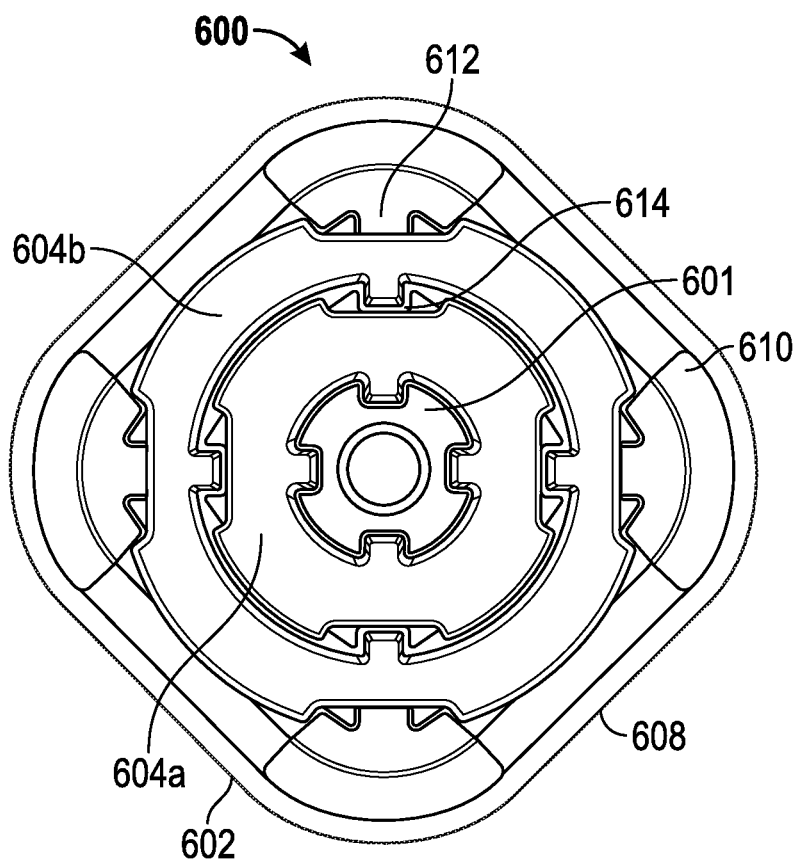
FIG. 38A
FIG. 38B

DILATION SYSTEM

CROSS REFERENCE TO RELATED APPLICATIONS

This application is a continuation of U.S. application Ser. No. 16/050,820, filed Jul. 31, 2018 which is a continuation of U.S. application Ser. No. 14/046,685, filed Nov. 1, 2012, now U.S. Pat. No. 10,039,540; which is a continuation-in-part of PCT/US2012/063061, filed Nov. 1, 2012; which claims benefit to U.S. Provisional Application Ser. No. 61/554,397, filed Nov. 1, 2011; the entire contents of each being hereby incorporated herein by reference.

BACKGROUND OF THE PRESENTLY DISCLOSED INVENTIVE CONCEPTS

1. Field of the Presently Disclosed Inventive Concepts

The inventive concepts disclosed and claimed herein relate to systems and methods for performing surgical procedures and, more particularly, but not by way of limitation, to systems and methods for accessing a surgical target site to perform surgical procedures.

2. Brief Description of Related Art

The present state of the art, when referencing a lateral surgical access approach, typically consists of using the following surgical instruments: neuromonitoring probe, dilators, and a retractor. Once an operative level is identified and an incision is created, dilators are used to create a surgical access site which is often followed by the use of a retractor or other specialized tools to create a surgical access corridor.

During a lateral approach to a patient's spine, a psoas muscle, which is located on either side of the spine, is separated in order to access the spine and, in particular, an intervertebral disc space or one or more vertebral bodies within a patient's spinal column. It is desirable to avoid neural elements or nerves of the lumbar plexus that lie within the psoas muscle during such procedures. The anterior third of the psoas muscle is typically considered a safe zone for muscle separation.

The neural elements or nerves of the psoas muscle may be mapped using a stimulating probe. In this manner, the most posterior neural or nerve free area of the psoas muscle may be located and identified. The stimulating probe may then be inserted through the psoas muscle via the most posterior neural or nerve free tissue area or through nearly any other region that is free of neural elements or nerves and toward the spine or into the intervertebral disc space in order to initiate safe tissue separation of the psoas muscle. Dilators are next placed over the probe to create and enlarge a surgical access site. Following the use of dilators, a retractor or other specialized tools are used to further enlarge the surgical access corridor.

Concentric dilators separate the muscle radially, and as such, dilate tissue on all both sides of the stimulating probe in a uniform fashion. This in turn may impinge on neural elements or nerves located outside of the safe zone. Directional dilators have been suggested to overcome the problems associated with concentric dilators. While directional dilation systems are effective have avoiding known neural elements, they are limited in their ability to continuously monitor nerve proximity and to create a surgical access site of a desired shape while at the same time reducing the amount of tissue damage.

BRIEF DESCRIPTION OF THE DRAWINGS

FIG. 11A is an elevational view of an exemplary first dilator of the dilation system of FIG. 7.

FIG. 11B is a top plan view of the first dilator.

FIG. 12A is an elevational view of an exemplary second dilator of the dilation system of FIG. 7.

FIG. 12B is a top plan view of the second dilator.

FIG. 14 is a perspective view of another embodiment of a dilation system constructed in accordance with the inventive concepts disclosed herein.

FIG. 15A is a perspective view of an exemplary first dilator shown being inserted over a stimulating probe.

FIG. 15B is a perspective view of an exemplary second dilator being inserted over the first dilator.

FIG. 15C is a perspective view of an exemplary third dilator being inserted over the first dilator.

FIG. 16A is a front elevational view of the first dilator of the dilation system of FIG. 14.

FIG. 16B is a side elevatonal view of the first dilator.

FIG. 16C is a rear elevational view of the first dilator.

FIG. 16D is a sectional view taken along line 16D-16D of FIG. 16C.

FIG. 17 is a sectional view taken along line 17-17 of FIG. 16B.

FIG. 18 is top end view of the first dilator.

FIG. 19 is a front elevational view of an exemplary second dilator of the dilation system of FIG. 14.

FIG. 20A is a sectional view taken along line 20A-20A of FIG. 19.

FIG. 20B is a sectional view taken along line 20B-20B of FIG. 19.

FIG. 21 is a front elevational view of an exemplary third dilator of the dilation system of FIG. 14.

FIG. 22A is a sectional view taken along line 22A-22A of FIG. 21.

FIG. 22B is a sectional view taken along line 22B-22B of FIG. 21.

FIG. 24A is a perspective view of another embodiment of a dilation system constructed in accordance with the inventive concepts disclosed herein shown in a closed condition.

FIG. 24B is a perspective view of the dilation system of FIG. 24A shown in an expanded condition.

FIG. 25 is a sectional view taken along line 25-25 of FIG. 24B.

FIG. 26 is an exploded, perspective view of a link assembly.

FIG. 36A is an elevational view of another embodiment of a dilation system constructed in accordance with the inventive concepts disclosed herein.

FIG. 36B is a top end view of the dilation system of FIG. 36A.

FIG. 37A is an elevational view of the dilation system of FIG. 36A shown with a first expansion member.

FIG. 37B is a top end view of the dilation system of FIG. 37A.

FIG. 38A is an elevational view of the dilation system of FIG. 37A shown with a second expansion member.

FIG. 38B is a top end view of the dilation system of FIG. 38A.

DETAILED DESCRIPTION OF EXEMPLARY EMBODIMENTS

Figure 1:
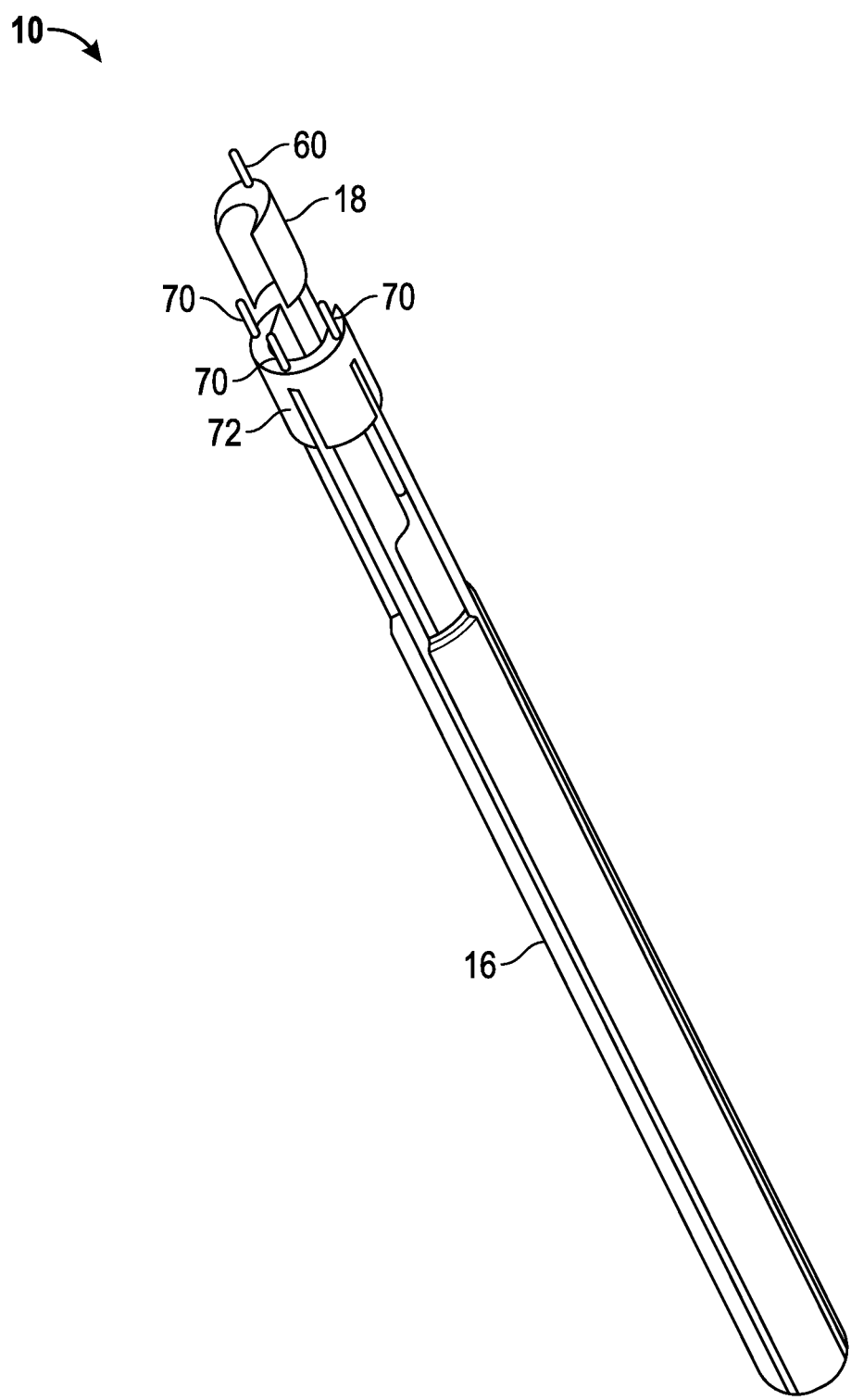
FIG. 1 is a partially exploded, perspective view of a dilation system constructed in accordance with the inventive concepts disclosed herein having three dilators and three electrode assemblies.

Before explaining at least one embodiment of the presently disclosed and claimed inventive concepts in detail, it is to be understood that the presently disclosed and claimed inventive concepts is not limited in its application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

Certain exemplary embodiments of the invention will now be described with reference to the drawings. In general, such embodiments relate to dilation systems for accessing a patient's spinal column.

As generally understood by one of ordinary skill in the art, the dilation systems will be described in connection with accessing the spine to perform a surgical procedure, but the dilation systems will find use not only in orthopedic surgery, but in other surgical procedures in which a surgeon wishes to gain access to an internal cavity by cutting the skin and going through the body wall in order to keep the incision spread apart so that surgical instruments can be inserted. For example, the dilation systems may be used for anteriorly or posteriorly accessing the spine, for accessing the thoracic or cervical region of the spine, or for accessing nearly any other part of the body.

Referring to FIGS. 1-6, a dilation system 10 is illustrated. The dilation system 10 includes a plurality of sequential dilators 12, 14, and 16, and a plurality of electrode assemblies 18 and 20. The sequential dilation system 10 may include more or less dilators such as, for example, one, two four, etc. The dilation system 10 is adapted to be used in combination with a monitoring K-wire or stimulating probe (not shown) known for transmitting an electrical pulse.

Figure 4A:
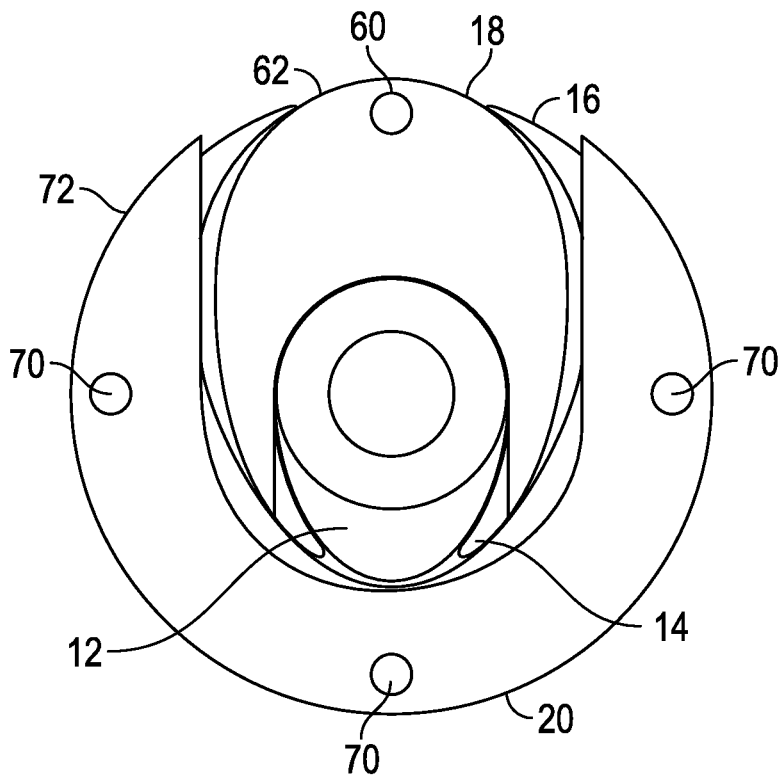
FIG. 4A is a top plan view of the dilation system.
Figure 4B:
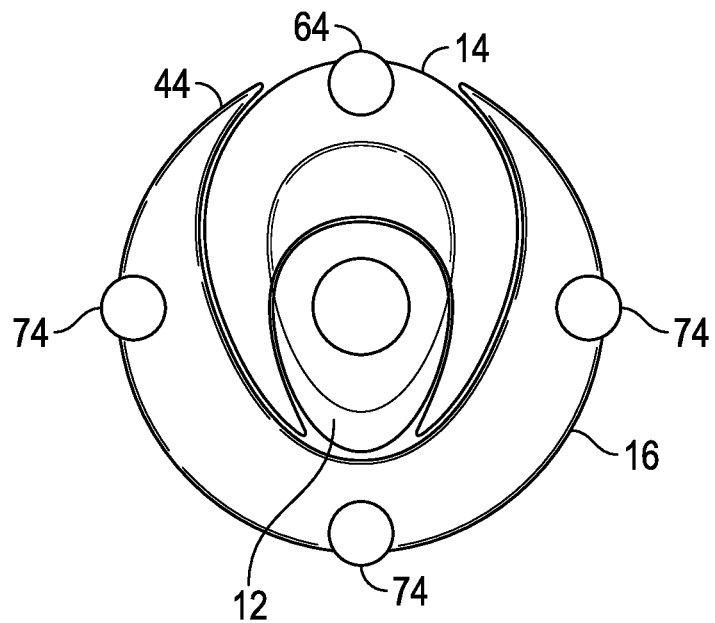
FIG. 4B is a bottom plan view of the dilation system.
Figure 4C:
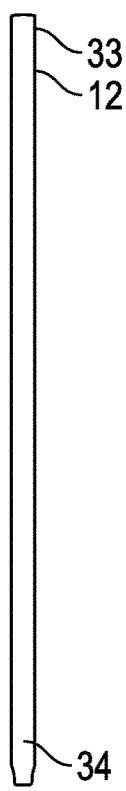
FIG. 4C is an elevational view of a first dilator.
Figure 4D:
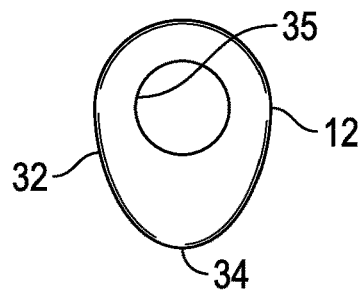
FIG. 4D is a top plan view of the first dilator.
Figure 4E:
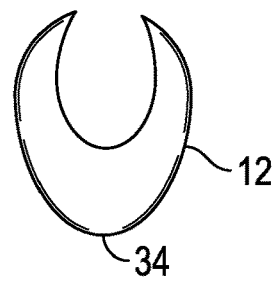
FIG. 4E is a top plan view of another embodiment of a first dilator.

Referring to FIGS. 4C-4E, 5A, and 5B, the first dilator 12 is a tubular member having an outer surface 32, a proximal end 33, a distal end 34 and a bore 35 extending from the proximal end 33 to the distal end 34. The first dilator is illustrated as having a substantially egg shaped transverse cross section whereby the first dilator 12 is provided with a lobe 36. The bore 35 is offset from the longitudinal axis of the first dilator 12 away from lobe 36. The bore 35 is sized to receive a stimulating probe (not shown). Alternatively, the first dilator 12 may be provided with a channel 38 formed near the tip of the lobe and extending the length of the first dilator 12 (FIG. 6), or the first dilator 12 may have an open side 37 opposite the lobe 36 (FIG. 4E).

In use, the first bore 35 removably receives the stimulating probe in an assembled configuration (e.g., when the stimulating probe is slidably received within the first bore 35 of the first directional dilator 12) so that a surgeon can stimulate the first dilator 12. The axis of the stimulating probe may be coaxial with the axis of the bore 35 of the first dilator 12 in the assembled configuration.

Figure 5A:
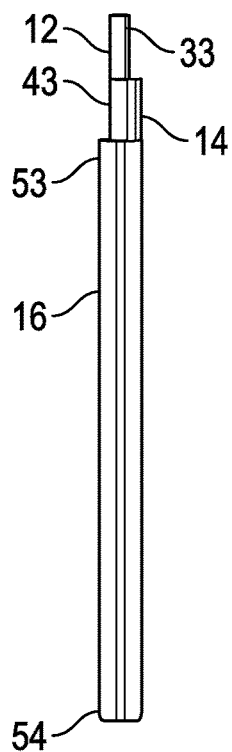
FIG. 5A is an elevational view of the dilators shown without the electrode assemblies and shown assembled in a concentric arrangement.
Figure 5B:
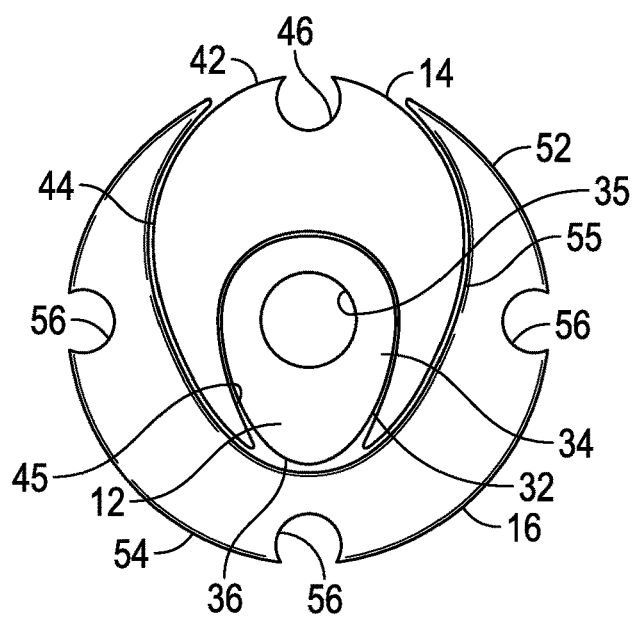
FIG. 5B is a bottom plan view of the dilators shown without the electrode assemblies and shown assembled in a concentric arrangement.

With reference to FIGS. 5A and 5B, the second dilator 14 is characterized as being an open sided tubular structure that has an outer surface 42, a proximal end 43, a distal end 44, and a bore 45 extending from the proximal end 43 to the distal end 44. The second dilator 14 is illustrated as having a substantially oval shaped transverse cross section. The bore 45 is offset from the longitudinal axis of the second dilator 14 toward the open side of the second dilator 14. The bore 45 is shaped to slidingly receive the first dilator 12 so that the tip of the lobe 36 of the first dilator 12 is received in the open side of second dilator 14 and is substantially flush with the outer surface of the second dilator 14. The second dilator 14 further includes a channel 46 formed at or near the outer surface 42 of the closed side of second dilator 14 extending the length of the second dilator 14 (FIG. 6) for receiving an electrode in a manner to be described below. Because the bore of the second dilator 14 is offset toward the lobe 36 of the first dilator, inserting the second dilator 14 over the first dilator 12 causes the second dilator 14 to dilate the opening formed in the patient in a direction opposite the lobe 36 of the first dilator 12.

The third dilator 16 is characterized as being an open sided tubular structure that has an outer surface 52, a proximal end 53, a distal end 54 and a bore 55 extending from the proximal end 53 to the distal end 54. The third dilator 16 is illustrated as having a substantially circularly shaped transverse cross section. The bore 54 is offset from the longitudinal axis of the third 16 dilator toward the open side of the third dilator 16. The bore 55 is shaped to slidingly receive the second dilator 12. As such, in the exemplary embodiment, the bore 55 is oval shaped. The third dilator 16 further includes a plurality of channels 56 formed at or near outer surface of the third dilator 14 extending the length of the second dilator 14 (FIG. 6) for receiving electrodes in a manner to be described below.

Figure 6:
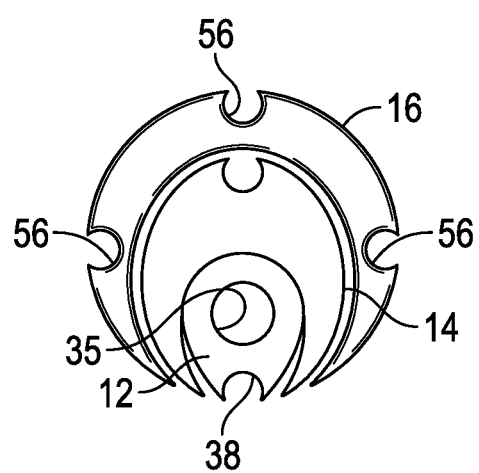
FIG. 6 is a bottom plan view of the dilators without the electrode assemblies and shown arranged in an eccentric arrangement.

Because the bore 54 is oval shaped, the third dilator 16 may be inserted over the second dilator 14 in one of two ways. First, as illustrated in FIG. 5B, the third dilator 16 may be inserted over the second dilator 14 with the open side of the third dilator 16 positioned opposite the open side of the second dilator 14. This causes the opening formed in the patient by insertion of the third dilator 16 to be concentrically positioned about the bore 35 of the first dilator 12. Second, as illustrated in FIG. 6, the third dilator 16 may be inserted over the second dilator 14 with the open side of the third dilator 16 positioned in alignment with the opposite the open side of the second dilator 14. This causes the opening formed in the patient by insertion of the third dilator 16 to be eccentrically positioned about the bore 35 of the first dilator 12 or in a direction away from the bore 35 of the first dilator 12.

Referring again to FIGS. 1-3, the electrode assembly 18 includes an electrode 60 and an electrode holder 62. The electrode 60 can be any electrode now or hereafter known for transmitting an electrical pulse. The electrode 60 includes an electrode tip 64 (FIG. 4B). The electrode holder 62 is formed of an electrically insulating material and is substantially similar in shape to the second dilator 14 so as to be positionable about a portion of the first dilator 12. The electrode 60 extends through the electrode holder 62 so that a proximal end of the electrode 62 extends from an upper end of the electrode holder 62.

In use, the electrode holder 62 may function as a handle to facilitate insertion of the electrode 60 into the channel 46 of the second dilator 14 until the electrode holder 62 contacts the proximal end of the second dilator 14 and the electrode tip 64 is position near the distal end 44 of the second dilator 14 (FIG. 4B).

The electrode assembly 18a includes three electrodes 70 and an electrode holder 72. The electrodes 70 can be any electrode now or hereafter known for transmitting an electrical pulse. The electrodes 70 include an electrode tip 74. The electrode holder 72 is substantially similar in shape to the third dilator 14 so as to be positionable about a portion of the second dilator 14. The electrodes extend through the electrode holder 72 so that a proximal end of the electrodes 70 extends from an upper end of the electrode holder 72.

Figure 2:
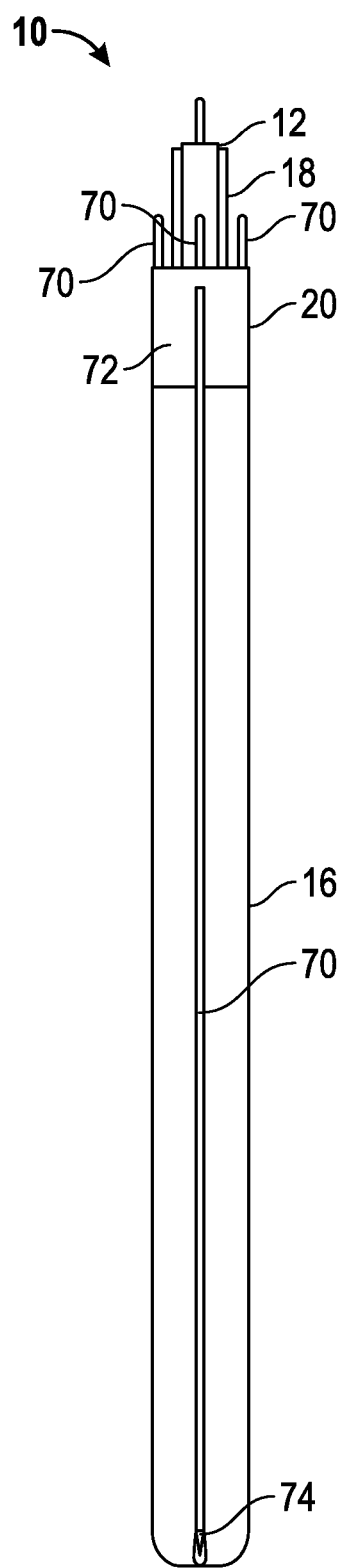
FIG. 2 is an elevational view of the dilation system of FIG. 1.
Figure 3:
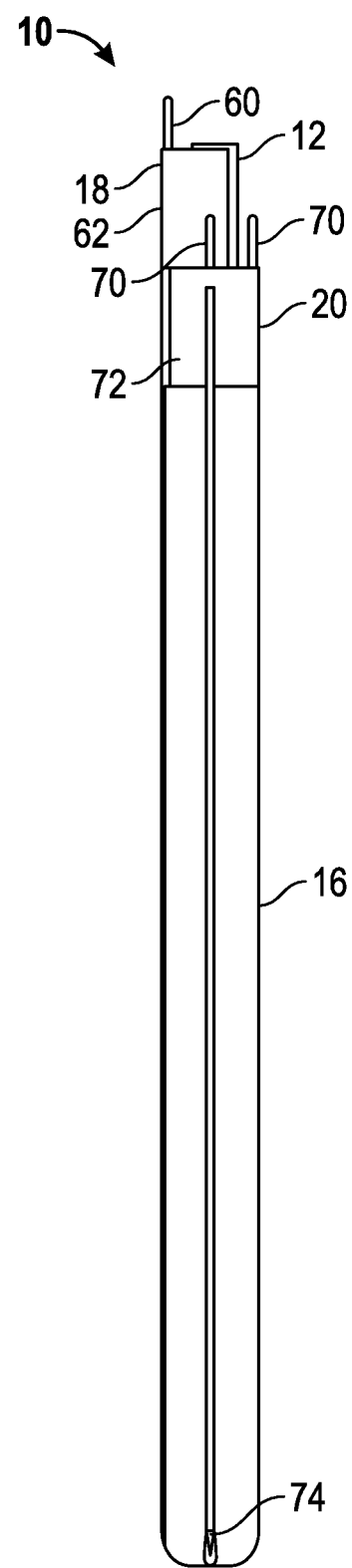
FIG. 3 is an elevational view of the dilation system of FIG. 2 shown rotated 90 degrees.

In use, the electrode holder 72 may function as a handle to facilitate insertion of the electrodes into the channels 56 of the third dilator 16 until the electrode holder 72 contacts the proximal end of the third dilator 16 and the electrode tips 74 are position near the distal end of the third dilator 16 (FIGS. 2, 3, and 4B).

The dilation system 10 is shown to use four electrodes to determine nerve location during the preparation of a surgical corridor. Four electrodes at final assembly allow nerves to be located 360° around the surgical site without the additional step of rotating the dilators. The assembly procedure would be carried out one dilator at a time with the first dilator 12 placed over a stimulating probe. Once the first dilator 12 is in place, the probe may be removed and replaced with a K-wire, if desired. The second dilator 14 with a single disposable electrode attached is placed over both the first dilator 12 and k-wire. The single electrode can be utilized to determine nerve proximity and the assembly can be rotated as one unit. The third dilator 16 is placed over all the elements with three additional disposable electrodes attached. Once fully assembled, the third and second dilators place the four electrodes 90° apart allowing for nerve detection in four equally separated directions spanning 360°.

Additionally, the eccentric dilators are shaped in an oblong fashion to prevent rotation between elements and allow for a unique assembly orientation. The dilator assembly can be rotated at each step without causing damage to surrounding tissue as a result of rotating interfaces and eliminates the possibility of single electrode misplacement relative to the triple electrodes. This feature ensures that the four electrodes are placed 90° apart at final assembly and unwanted rotation between dilators does not occur during use.

The shape of the dilators can be made so the dilators are assembled in an alternating pattern, which allows for the k-wire channel to be located concentric to the final assembly. As well, the dilators can be assembled in an eccentric pattern, allowing for dilation to occur in tissue in a single direction. This can be advantageous to perform dilation in a direction away from nerve tissue.

Rotation between dilators can be eliminated via a keyhole slot, locking method or other geometry. Greater or fewer dilatation steps can be used. Electrodes can be integrated into the dilators for greater than one time use. Electrodes can be placed in an alternative pattern. Electrodes can be assembled in different combinations (e.g., two sets of two electrodes, four single electrodes, only two electrodes etc). Greater or fewer electrodes can be used. Dilator assembly could have a non-circular basis.

Referring now to FIGS. 7-13, another embodiment of a dilation system 10a is illustrated. The dilation system 10a includes a plurality of sequential dilators 12a, 14a, and 16a. The sequential dilation system 10a may include more or less dilators such as, for example, one, two four, etc. The dilation system 10a is adapted to be used in combination with a monitoring K-wire or stimulating probe (not shown) known for transmitting an electrical pulse.

As best shown in FIGS. 11A and 11B, the first dilator 12a is characterized as being an open sided tubular structure having an outer surface 32a, a proximal end 33a, a distal end 34a, and a bore 35a extending from the proximal end 33a to the distal end 34a. The first dilator 12a is illustrated as being substantially oval shaped. The bore 35a is offset from the longitudinal axis of the first dilator 12a. The bore 35a is sized to receive a K-wire (not shown). The first dilator 12a is provided with an electrode 38 at the distal end 34a generally opposite the bore 35a. The first dilator 12a further has a corresponding connector point 39 (FIG. 11A) for connecting the electrode to neural monitoring equipment.

As best shown in FIGS. 12A and 12B, the second dilator 14a is characterized as being an open sided tubular structure having an outer surface 42a, a proximal end 43a, a distal end 44a, and a bore 45a extending from the proximal end 43a to the distal end 44a. The second dilator 14a is illustrated as having a substantially oval shaped transverse cross section. The bore 45a is offset from the longitudinal axis of the second dilator 14a toward the open side of the second dilator 14a. The bore 45a is shaped to slidingly receive the first dilator 12a so that one side of the first dilator 12a is received in the open side of second dilator 14a and is substantially flush with the outer surface of the second dilator 14a. Alternatively, the second dilator 14a can be positioned over the first dilator 12a with the open sides aligned. The second dilator 14a is provided with an electrode 48 at the distal end generally opposite the bore 45a. The second dilator 14a further has a corresponding connector point 49 for connecting the electrode to neural monitoring equipment.

Figure 9:
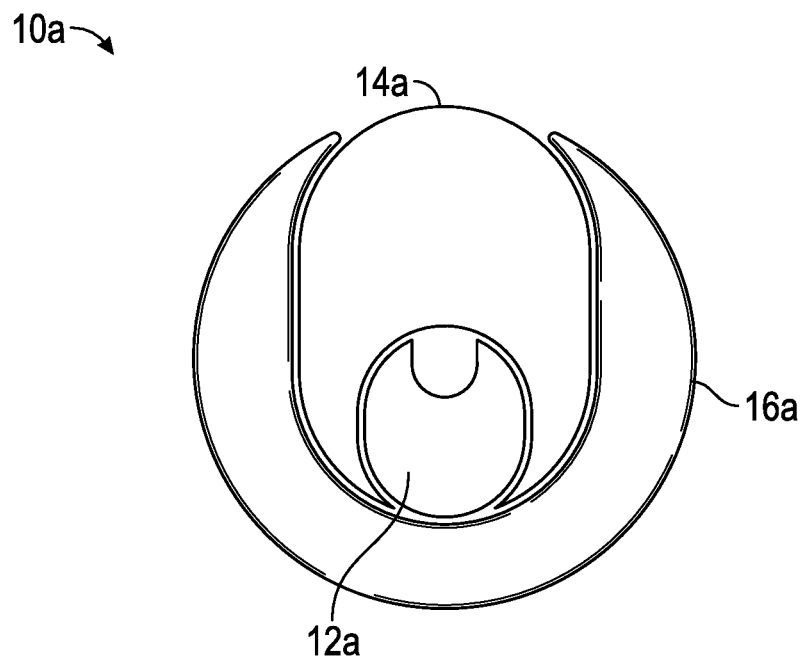
FIG. 9 is a top plan view of the dilation system of FIG. 7 shown in a concentric arrangement.
Figure 10:
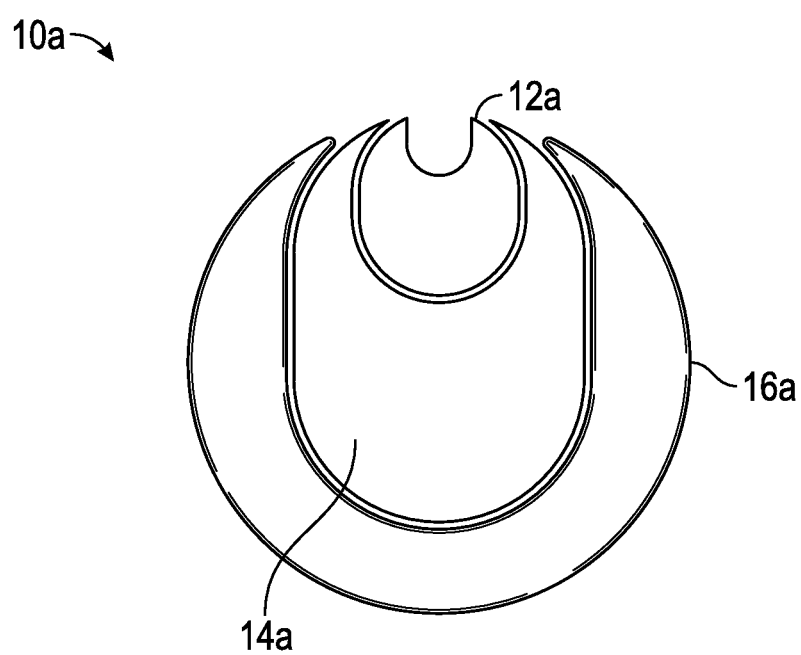
FIG. 10 is a top plan view of the dilation system of FIG. 7 shown in an eccentric arrangement.
Figure 13A:
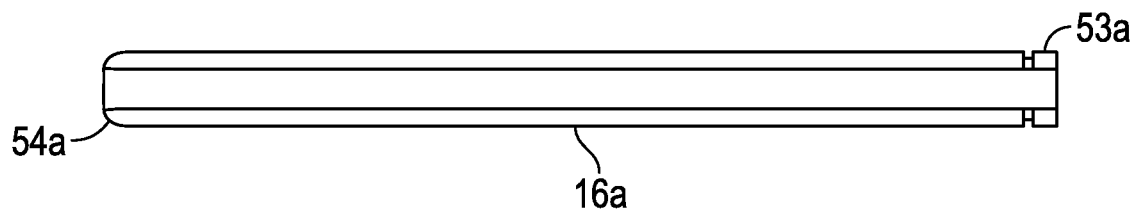
FIG. 13A is an elevational view of an exemplary third dilator of the dilation system of FIG. 7.
Figure 13B:
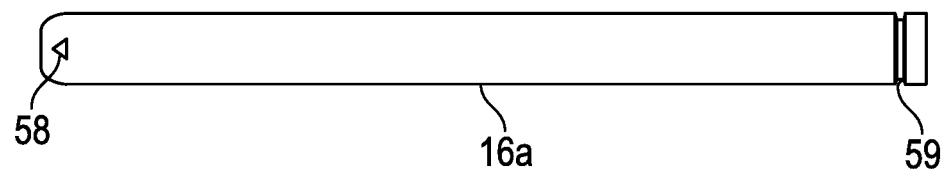
FIG. 13B is an elevational view of the third dilator of FIG. 13A shown rotated 90 degrees.
Figure 13C:
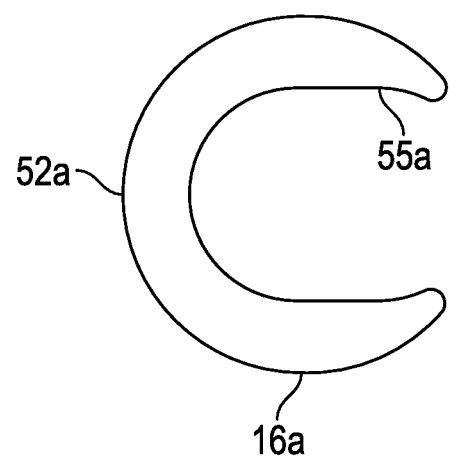
FIG. 13C is a top plan view of the third dilator.

Referring now to FIGS. 13A and 13B, the third dilator 16a is characterized as being an open sided tubular structure that has an outer surface 52a, a proximal end 53a, a distal end 54a, and a bore 55a extending from the proximal end 53a to the distal end 54a. The third dilator 16a is illustrated as having a substantially circularly shaped transverse cross section. The bore 55a is offset from the longitudinal axis of the third dilator 16a toward the open side of the third dilator 16a. The bore 55a is shaped to slidingly receive the second dilator 12a. As such, the bore is oval shaped. Because the bore is oval shaped, the third dilator 16a may be inserted over the second dilator 14a in one of two ways. First, as illustrated in FIG. 9, the third dilator 16a may be inserted over the second dilator 14a with the open side of the third dilator 16a positioned opposite the open side of the second dilator 14a. This causes the opening formed in the patient by insertion of the third dilator 16a to be concentrically positioned about the bore of the first dilator 12a. Second, as illustrated in FIG. 10, the third dilator 16a may be inserted over the second dilator 14a with the open side of the third dilator 16a positioned in alignment with the opposite the open side of the second dilator 14a. This causes the opening formed in the patient by insertion of the third dilator 16a to be eccentrically positioned about the bore of the first dilator 12a or in a direction away from the bore of the first dilator 12a. The third dilator 16a is provided with an electrode 58 at the distal end generally opposite the bore 55a. The third dilator 16a further has a corresponding connector point 59 for connecting the electrode to neural monitoring equipment.

The electrodes of the first, second, and third dilators 12a, 14a, and 16a are provided for the purpose of determining the location of nerves or neural structures relative to the each of the dilators 12a, 14a, and 16a as they are advanced over the K-wire towards or positioned at or near the surgical target site. The dilators 12a, 14a, and 16a may be equipped with the electrodes via any number of suitable methods, including but not limited to providing electrically conductive elements within the walls of the dilators such as by manufacturing the dilators from plastic or similar material capable of injection molding or manufacturing the dilators from aluminum (or similar metallic substance) and providing outer insulation layer with exposed regions (such as by anodizing the exterior of the aluminium dilator).

Figure 7:
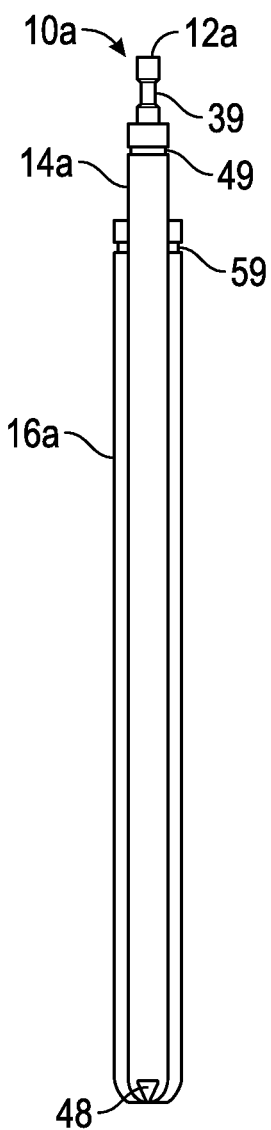
FIG. 7 is an elevational view of another embodiment of a dilation system constructed in accordance with the inventive concepts disclosed herein having three dilators.
Figure 8:
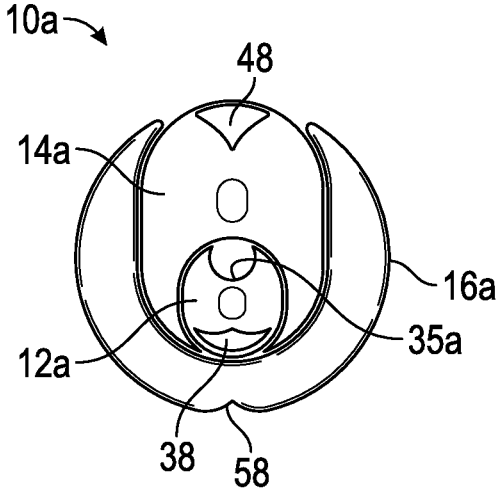
FIG. 8 is a bottom plan view of the dilation system of FIG. 7.

As best shown in FIGS. 3 and 7, the first dilators 12 and 12a have a length greater than the length of the second dilator 14 and 14a, respectively, and the second dilators 14 and 14a have a length greater than the length of the third dilators 16 and 16a, respectively. This stepped arrangement permits the proximal ends of the first dilators 12 and 12a to extend further out of the patient in the assembled and operational configurations to facilitate connection of the electrodes to the neural monitoring equipment and such that a surgeon may grasp and remove or otherwise manipulate the dilators.

It should be understood that the dilators described above may include a plurality of depth indicators located on the outer surface thereof.

A method of using the dilation systems 10 and 10a will now be described for accessing a patient's spine. The technique may be particularly desirable for accessing the lumbar region of the spine via a lateral approach, although a similar or the same method may be used in other parts of the patient's body.

Using a stimulating probe and an electromyograph (EMG) (not shown) in a manner similar to that described in U.S. 2011/0208226 and U.S. Ser. No. 13/887,838, which is hereby expressly incorporated herein by reference, the surgeon may map a safe zone, i.e., a zone generally free of any neural elements or nerves, on the tissue of interest (e.g., psoas muscle). For example, on the psoas muscle, the anterior third of the psoas muscle is generally considered a safe zone.

Once a safe zone is established, anatomical placement may be confirmed via intra-operative fluoroscopy. The surgeon inserts the stimulating probe through the psoas muscle toward the patient's spine. If the surgery is being performed on the intervertebral disc space, the distal end of the stimulating probe may be inserted into the annulus of the desired intervertebral disc space. The stimulating probe may be inserted via the most posterior portion of the safe zone.

The surgeon can insert or slide the first dilator 12, 12a over the stimulating probe so that the first longitudinal axis is located to one side of the stimulating probe, away from a sensed neural element or nerve, through the psoas muscle and into a position proximate the patient's spine. The surgeon can then insert the second dilator 14, 14a, if necessary, to further dilate the tissue proximate the outside surface of the first dilator 12, 12a and in a desired direction. The surgeon can repeat this process as often as necessary. Finally, if desired, a retractor (not shown) can be inserted over the third dilator 16, 16a to subsequently retract the tissue and to permit removal of the dilation system 10, 10a and the stimulating probe.

Referring now to FIG. 14, another embodiment of a dilation system 100 is illustrated. The dilation system 100 includes a plurality of sequential dilators 112, 114, and 116. The dilation system 100 may include more or less dilators such as, for example, one, two four, etc. The dilation system 100 is adapted to be used in combination with a monitoring K-wire or stimulating probe 118 known for transmitting an electrical pulse.

Referring now to FIGS. 15A, 16A-16D, 17, and 18, the first dilator 112 is an elongated, tubular member having an outer surface 120, a proximal end 122, a distal end 124 and a bore 126 extending from the proximal end 122 to the distal end 124. The bore 126 is sized to receive the stimulating probe 118. The first dilator 112 may be provided with a second bore or channel 138 extending parallel to the bore 126 and the length of the first dilator 112 for receiving an electrode 140.

The first dilator 112 is further characterized as having a lower section 128, an upper section 130, and an intermediate section 132. The lower section 128 is sized and configured to be extended through the psoas muscle. By way of example, the lower section 128 may have a diameter in a range of from about 4 mm to about 10 mm. In one embodiment, the lower section 128 has a generally keyhole shaped cross section.

The upper section 130 of the first dilator 112 is provided with a first guide 134 and a second guide 136 which are configured to slidably and matingly engage with the second dilator 114 and the third dilator 116, respectively, in a manner to be discussed below. The first guide 134 is illustrated has having a dovetail configuration with a taper at a proximal end thereof to facilitate engagement with the second dilator 114. Similarly, the second guide 136 is illustrated as having a dovetail configuration with a taper at a proximal end thereof to facilitate engagement with the third dilator 116. In one embodiment, the first guide 134 and the second guide 136 extend radially outwardly in diametrically opposing directions.

It should be appreciated that the first guide 134 and the second guide 136 may be formed in a variety of shapes. For example, the first guide 134 and the second guide 136 may be formed as grooves configured to receive a dovetail tongue. Also, the first guide and the second guide may be formed so that the size of the first guide 134 is different from the size of the second guide 136 for reasons that will be described below.

The intermediate section of the first dilator 112 may be an open sided structure, and shaped similar to the lower section 128 (e.g., generally keyhole shaped cross section). As illustrated in FIG. 16D, the first dilator 112 may be constructed in multiple pieces. For example, the lower section 128, the upper section 130, and the intermediate section 132 may be formed as separate pieces which are adapted to be assembled with one another. It will also be understood that the first dilator 112 may be formed as a single piece.

With reference to FIGS. 15B, 19, 20A, and 20B, the second dilator 114 is configured to slide along the first dilator 112 (FIG. 15B) and be positioned to create a semicircular cross section that assists with slitting muscle fibers when a combination of the first dilator 112 and the second dilator 114 are rotated about the stimulated probe 118. The second dilator 114 is generally characterized as being an elongated, open sided or C-shaped structure that has an outer surface 141, an inner surface 142, a proximal end 143, a distal end 144, and a bore 145 extending from the proximal end 143 to the distal end 144 for receiving an electrode, such as the electrode 140, in a manner to be described below.

The second dilator 114 is further characterized as having a lower section 146, an upper section 148, and an intermediate section 150. The inner surface 142 of the lower section 146 is sized and configured to be matingly received over a corresponding portion of the lower section 128 of the first dilator 112. The inner surface 142 of the upper section 148 of the second dilator 114 is configured to slidably and matingly engage with the first guide of the first dilator 112. To this end, the upper section 148 of the second dilator 114 has a groove 152 corresponding to the shape of the first guide 134. Again, it will be appreciated that the first guide 134 and the groove 152 may be formed in a variety of shapes and that the position of the first guide 134 and the groove may interchanged. To facilitate sliding of the second dilator 114 over the first dilator 112, the inner surface 142 of the intermediate section 150 of the second dilator 114 may be configured so that the inner surface 142 is in a non-contact relationship with the outer surface 120 of the first dilator 112.

The second dilator 114 has a first longitudinal edge 154 and a second longitudinal edge 156. The bore 145 may be formed proximate to the first longitudinal edge 154. The second longitudinal edge 156 may be angled to form a wedge with the inner surface 142 of the second dilator 114 to facilitate rotation of the first dilator 112 and the second dilator 114 relative to the muscle fiber.

With reference to FIGS. 15C, 21, 22A, 22B, the third dilator 116 is configured to slide along the first dilator 112 and be positioned to transform the semi-circular cross section of the combination of the first dilator 112 and the second dilator 114 to a circular cross section of a selected diameter, e.g. 16 mm-22 mm. The third dilator 116 is generally characterized as being an elongated, open sided or C-shaped structure that has an outer surface 160, an inner surface 162, a proximal end 164, a distal end 166 and a bore 168 extending from the proximal end 164 to the distal end 166 for receiving an electrode, such as the electrode 140, in a manner to be described below.

The third dilator 116 is further characterized as having a lower section 170, an upper section 172, and an intermediate section 174. The inner surface 162 of the lower section 172 is sized and configured to be matingly received over a corresponding portion of the lower section 128 of the first dilator 112. The inner surface 162 of the upper section 174 of the third dilator 116 is configured to slidably and matingly engage with the second guide 136 of the first dilator 112. To this end, the upper section 174 of the third dilator 116 has a groove 176 corresponding to the shape of the second guide 136. Again, it will be appreciated that the second guide 136 and the groove 176 may be formed in a variety of shapes and that the position of the second guide 136 and the groove 176 may be interchanged. To facilitate positioning of the third dilator 116 over the first dilator 112, the inner surface 162 of the intermediate section 176 of the third dilator 116 may be configured so that the inner surface 162 is in a non-contact relationship with the outer surface 120 of the first dilator 112.

The third dilator 116 has a first longitudinal edge 178 and a second longitudinal edge 180. The bore 168 may be formed proximate to the first longitudinal edge 178. The first longitudinal edge 178 and the second longitudinal edge 180 of the third dilator 116 are configured to mate with the second longitudinal edge 156 and the first longitudinal edge 154 of the second dilator 114, respectively. Because the first longitudinal edge 154 and the second longitudinal edge 156 of the second dilator 114 are angled to facilitate rotation within the psoas muscle, the first longitudinal edge 178 and the second longitudinal edge 180 of the third dilator 116 have an inverse shape to that of the first longitudinal edge 154 and the second longitudinal edge 156 of the second dilator 114 so as to mate with the first and second longitudinal edges 154 and 156 of the second dilator 114. To facilitate insertion of the second dilator 114 on the first dilator 112 prior to insertion of the third dilator 116, the first guide 134 and the second guide 136 may be sized differently from one another and the grooves 152 and 176 of the second and third dilators 114 and 116 may be sized to mate with the corresponding one of the first and second guides 134 and 136.

A method of using the dilation systems 100 will now be described for accessing a patient's spine. The technique may be particularly desirable for accessing the lumbar region of the spine via a lateral approach, although a similar or the same method may be used in other parts of the patient's body.

Using a stimulating probe 118 and an electromyograph (EMG) (not shown), a surgeon may map a safe zone, i.e., a zone generally free of any neural elements or nerves, on the tissue of interest (e.g., psoas muscle). For example, on the psoas muscle, the anterior third of the psoas muscle is generally considered a safe zone.

Once a safe zone is established, anatomical placement may be confirmed via intra-operative fluoroscopy. The surgeon inserts the stimulating probe 118 through the psoas muscle toward the patient's spine. If the surgery is being performed on the intervertebral disc space, the distal end of the stimulating probe 118 may be inserted into the annulus of the desired intervertebral disc space. The stimulating probe 118 may be inserted via the most posterior portion of the safe zone.

The surgeon can insert or slide the first dilator 112 over the stimulating probe 118, through the psoas muscle, and into a position proximate the patient's spine. The surgeon can insert a stimulating probe 140 into the bore 138 so that a surgeon can stimulate the first dilator 112 while the first dilator 112 is being inserted into position. The surgeon can then insert the second dilator 114 on the first dilator 112 by inserting the second dilator 114 laterally into to engagement with the first dilator 112 with the upper section of the second dilator 114 positioned above the first guide 134 of the first dilator 112 (FIG. 15B).

The second dilator 114 may then be slid downwardly along the first dilator 112 in such a way that the groove 152 of the second dilator 114 is received over the first guide 134 of the first dilator 112 so as to axially guide the second dilator 114 through the psoas muscle and further dilate the tissue. Prior to positioning the second dilator 114, the surgeon can remove the electrode 140 from the first dilator 112 and insert the electrode 140 into the bore 143 of the second dilator 114 to stimulate the second dilator 114 while the second dilator 114 is being inserted into position. The surgeon can repeat this process using the third dilator 116. Finally, if desired, a retractor can be inserted over the second dilator 114 and the third dilator 116 to subsequently retract the tissue and to permit removal of the dilation system 100 and the stimulating probe 118 and the electrode 140.

Figure 23A:
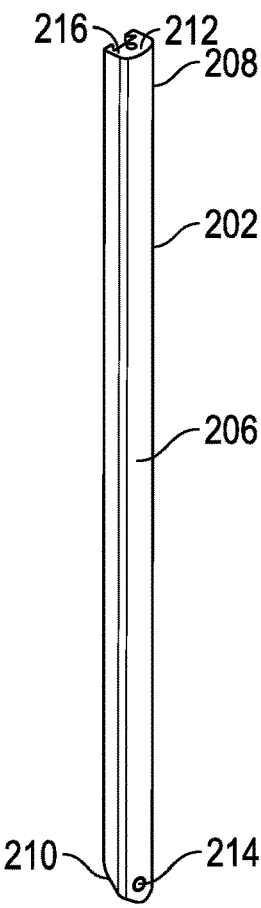
FIG. 23A is a perspective view of an exemplary first dilator of another embodiment of a dilation system.
Figure 23B:
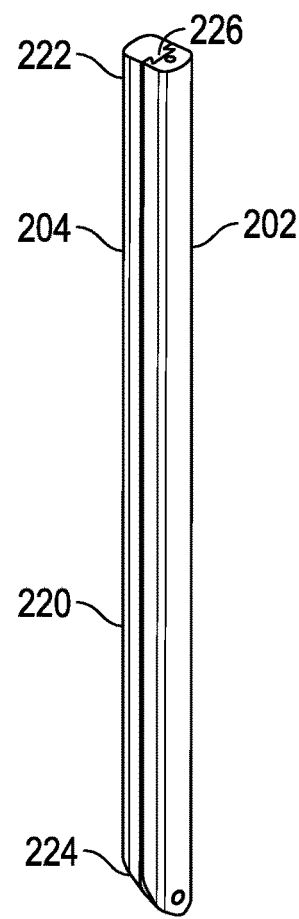
FIG. 23B is a perspective view illustration an exemplary second dilator connected to the first dilator.
Figure 23C:
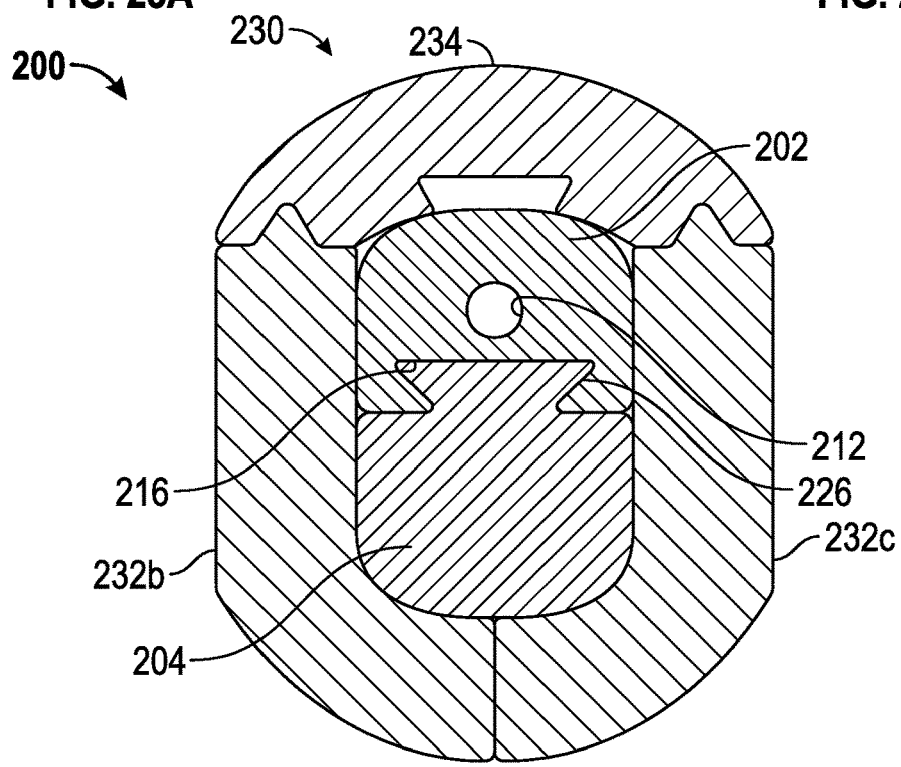
FIG. 23C is a sectional view of the first and second dilator shown in combination with a retractor assembly.
Figure 27A:
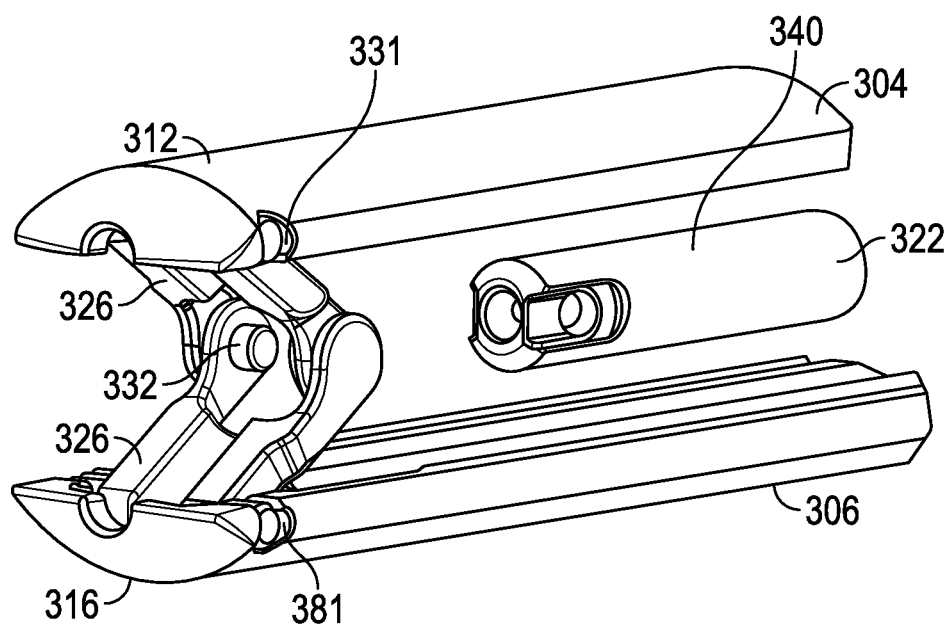
FIG. 27A is an exploded, perspective view of a drive rod shown detached from the link assembly.
Figure 27B:
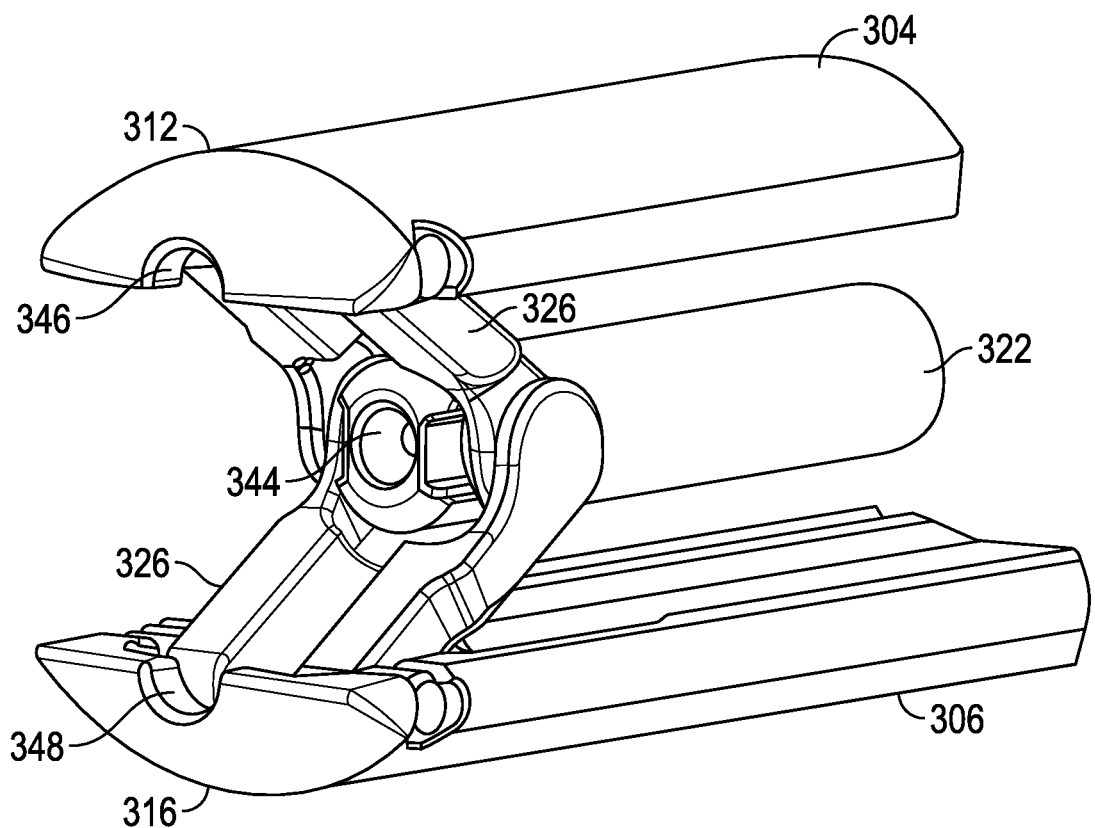
FIG. 27B is a perspective view of the drive shaft shown attached to the link assembly.

Referring now to FIGS. 23A-23C, another embodiment of a dilation system 200 is illustrated. The dilation system 200 includes a pair of dilators 202 and 204. The dilation system 200 may include more or less dilators such as, for example, one, three four, etc. The dilation system 200 is adapted to be used in combination with a monitoring K-wire or stimulating probe (not shown) known for transmitting an electrical pulse.

Referring now to FIG. 23A, the first dilator 112 is an elongated member having an outer surface 206, a proximal end 208, a distal end 210, and a bore 212 extending from the proximal end 208 to the distal end 210. The bore 212 is sized to receive a K-wire or stimulating probe, such as the stimulating probe 118 illustrated in FIG. 14. The first dilator 202 can be manufactured such that the K-wire can be accommodated via a continuous thru-bore or an open slot located closer to the outer surface of the first dilator 202.

The first dilator 202 is used to create the initial access corridor. The distal end 210 is tapered to facilitate insertion into tissue, and the distal end 212 is stimulatable via an exposed electrode 214. The general shape of the first dilator 202 is atraumatic. A connector 216 is provided along one side of the first dilator 202. The connector 216 is illustrated as being a dovetail groove.

In use, the first dilator 202 is inserted over the K-wire or stimulating probe with the connector 216 positioned in an anterior direction to monitor the proximity of nerves.

The second dilator 204 is used to further dilate tissue and can be advanced into position directly anterior to the first dilator 202. The second dilator 204 is an elongated member having an outer surface 220, a proximal end 222, and a distal end 224. Like the first dilator 202, the second dilator 204 may be manufactured with a stimulatable electrode. The shape of the second dilator 204 is atraumatic as it passes through tissue. The second dilator 204 is configured to connect to and slide along the length of the first dilator 202. To this end, the second dilator 204 has a connector 226.

The connector 226 of the second dilator 204 is configured for sliding and mating engagement with the connector 216 of the first dilator 202. In one embodiment, the connector 226 is a dovetail tongue that allows for the second dilator 204 to slide along the length of the first dilator 202 while maintaining attachment.

The dilation system 200 further includes a retractor blade assembly 230 (FIG. 23C) which is shown to include three blades 232a, 232b, and 232c. The contour of the blades 232a, 232b, and 232c, when assembled, closely matches the outer profile of a combination of the first dilator 202 and the second dilator 204. The posterior retractor blade 232a may have an embedded electrode and accompanying wiring to enable monitoring of nerves. The electrode and wiring can be embedded into the dilator blades and retractor blades or added afterwards by a sticky probe or conductive epoxy ink.

The dilators and the retractor blades can be machined, molded, or extruded and machined from materials such as stainless steel, anodized aluminum, PEEK, carbon fiber composite, or any biocompatible material suitable to maintain the shape and function of the components.

FIGS. 24-28 illustrate another embodiment of a dilation system 300 constructed in accordance with the inventive concepts disclosed herein. The dilation system 300 is used to create an initial corridor which may be expanded to a desired diameter, e.g., 16-22 mm, without inserting any additional instruments. In addition, the dilation system 300 is adapted to be used with a k-wire or stimulating probe, such as the stimulating probe 118 illustrated in FIG. 14. The dilation system 300 includes a base 302, a first blade 304, a second blade 306, and an actuating mechanism 308 operably associated with the first blade 304 and the second blade 306 so as to cause the first blade 304 and the second blade 306 to move from a closed condition (FIG. 24A) wherein the first blade 304 and the second blade 306 are positioned adjacent one another to permit insertion through selected tissue to an expanded condition (FIG. 24B) wherein the first blade 304 and the second blade 306 are spread apart relative to one another to expand the tissue.

The first blade 304 has a proximal end 310 and a distal end 312. The first blade 304 extends from the base 302 so that the distal end 312 of the first blade 304 extends away from the base 302 in such a way that the distal end 312 is deflectable relative to the proximal end 310. Similarly, the second blade 306 has a proximal end 314 and a distal end 316. The second blade 306 extends from the base 302 so that the distal end 316 of the second blade 306 extends away from the base 302 in such a way that the distal end 316 is deflectable relative to the proximal end 314. Each of the first blade 304 and the second blade 306 has a generally arcuate cross section and the distal ends 312 and 316 may be tapered to facilitate insertion into a patient. Each of the first blade 304 and the second blade 306 may be provided with a bore or channel (not shown) extending the length of the first dilator 112 for receiving an electrode (not shown) to aid in stimulating adjacent tissues.

The actuating mechanism 308 includes a linkage 320, a drive rod 322, and a drive member 324. In one embodiment, the linkage 320 includes a pair of cross links 326. Each cross link 326 is identical in construction and has a body 328 with a pin 330 pivotally connectable to the distal ends 312 and 316 of the first blade 304 and the second blade 306 via a groove 331 formed in the distal ends 312 and 316 of the first blade 304 and the second blade 306. Each cross link 326 further includes a pin 332 and hole 334 with the pin 332 being received through the hole 334 of the other cross link 326 and the hole 334 receiving the pin 332 of the other cross link 326. The body 328 is provided with a longitudinal groove 336 for receiving a stimulating probe when the first blade 304 and the second blade 306 are in the closed condition.

The drive rod 322 has a proximal end 338 and a distal end 340, and the drive rod 322 is positioned between the first blade 304 and the second blade 306. The distal end 340 of the drive rod 322 is provided with pair of holes 342 for pivotally receiving the pins 332 of the cross links 326 such that axial movement of the drive rod 322 moves the first blade 304 and the second blade 306 from the closed condition to the expanded condition.

The drive member 324 is rotatably connected to the base 302, and the proximal end 338 of the drive rod 322 is threadingly connected to the drive member 324 in such a way that rotational movement of the drive member 324 causes axial movement to the drive rod 322.

The drive member 324 and the drive rod 322 have a central bore 344 sized to receive a stimulating probe. Further, the distal end 312 of the first blade 304 may have a first notch 346, and the distal end 316 of the second blade 306 may have a second notch 348. The first notch 346 and the second notch 348 are aligned to cooperate to form an opening 350 (FIG. 24A) sized to receive the stimulating probe when the first blade 304 and the second blade 306 are in the closed condition.

Figure 28A:
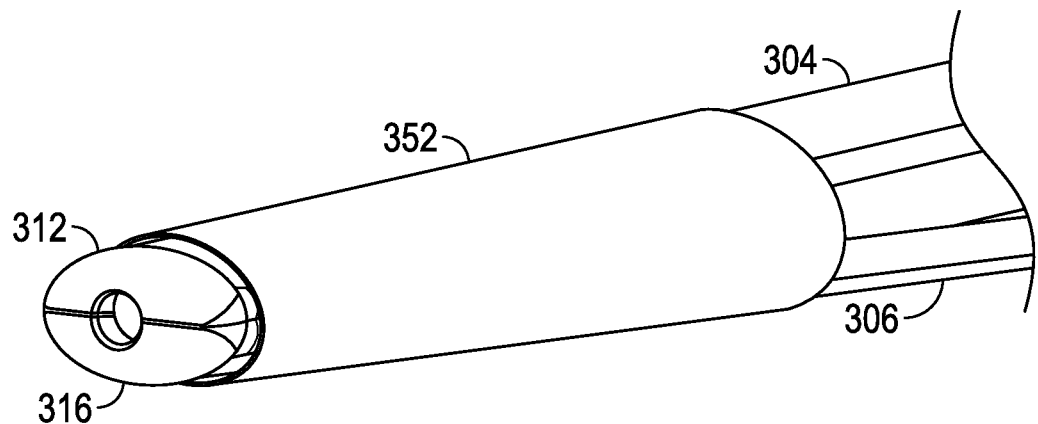
FIG. 28A is a perspective view of the dilation system of FIG. 14 illustrated in the closed condition provided with an expandable sheath.
Figure 28B:
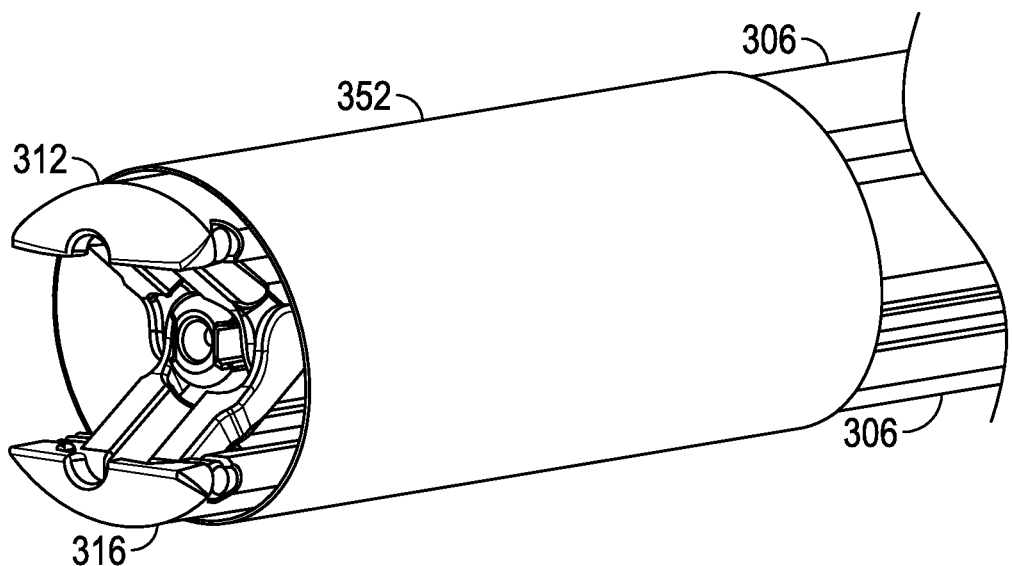
FIG. 28B is a perspective view of the dilation system of FIG. 28A shown in the expanded condition.
Figure 29:
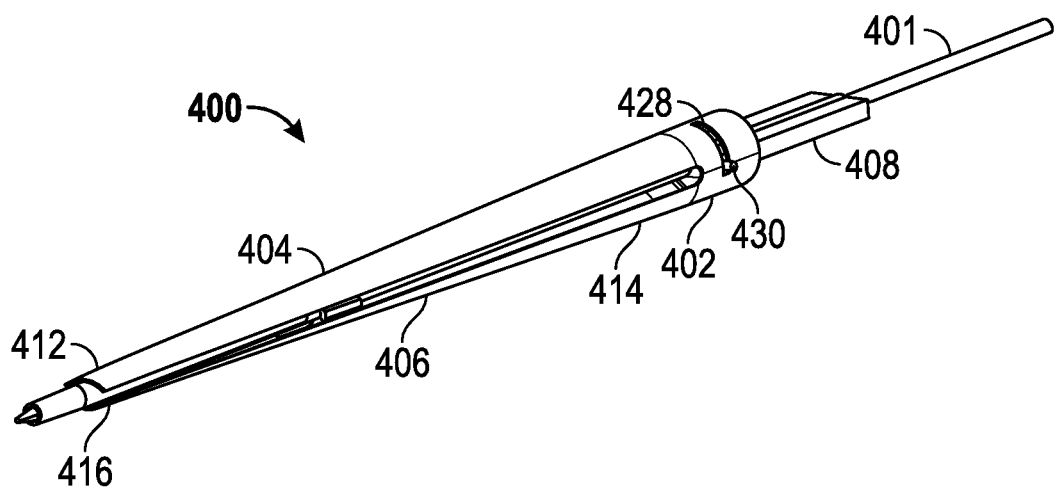
FIG. 29 is a perspective view of another embodiment of a dilation system constructed in accordance with the inventive concepts disclosed herein shown in a closed condition.
Figure 30:
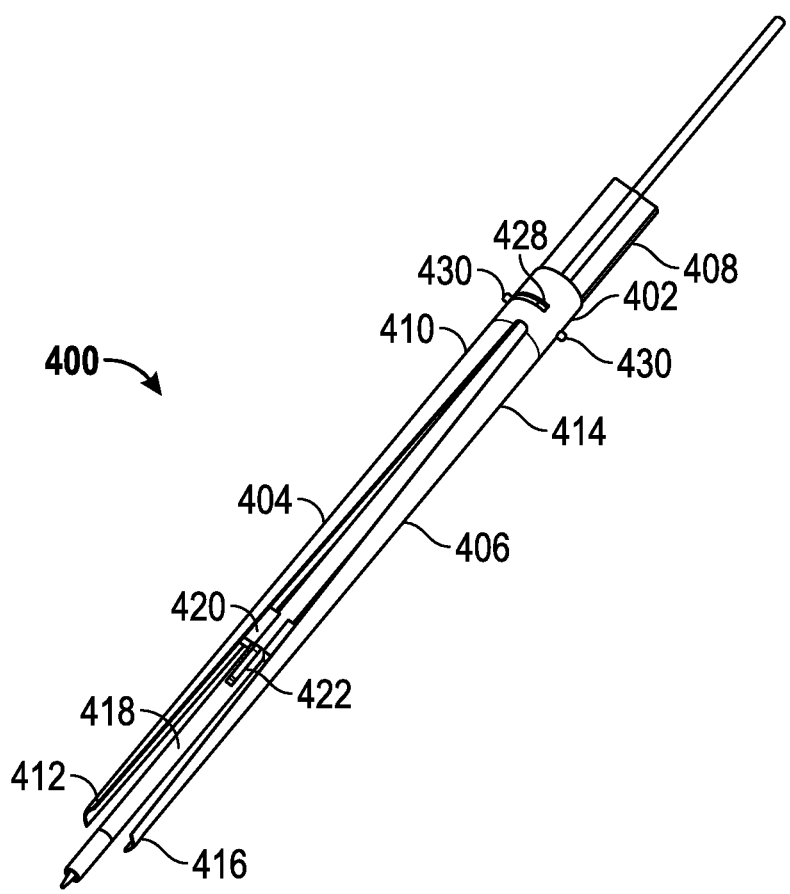
FIG. 30 is a perspective view of the dilation system of FIG. 28 shown in an expanded condition.
Figure 31:
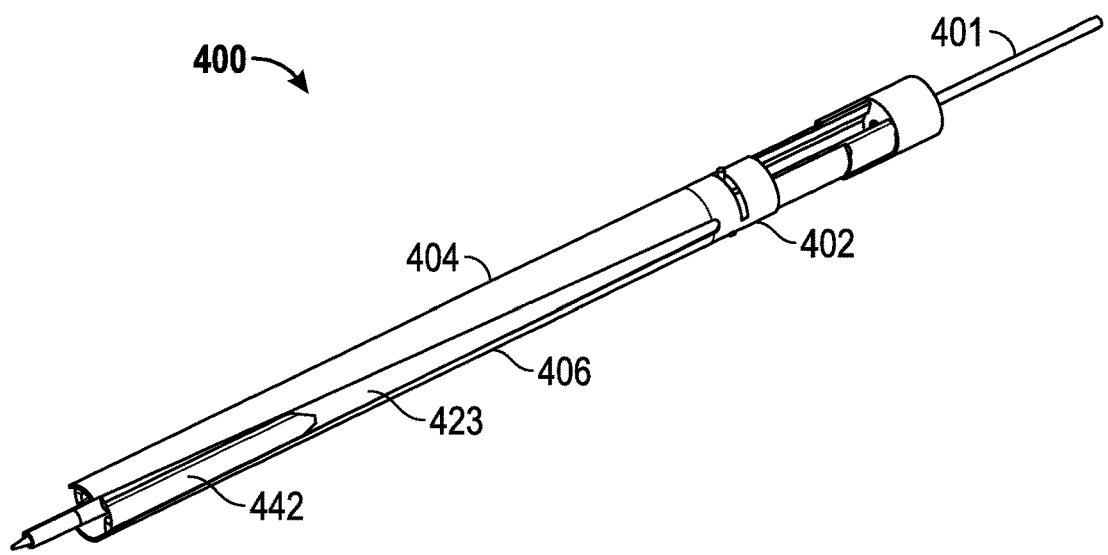
FIG. 31 is a perspective view of the dilation system of FIG. 28 shown in the expanded condition with a secondary expander shown inserted therein.

Referring to FIGS. 28A and 28B, the dilation system 300 may further include an expandable sheath 352 positioned about at least the distal ends of the first blade 304 and the second blade 306 to cover the spaces between the first blade 304 and the second blade 306. The sheath 352 can be made of any type of expandable material, such as a mesh, fabric, polymer, or elastomeric polymer.

Referring now to FIGS. 29-33, another embodiment of a dilation system 400 is illustrated. The dilation system 400 is used to create an initial corridor which may be expanded to a desired diameter, e.g., 16-22 mm, without inserting any additional instruments. In addition, the dilation system 400 is adapted to be used with a k-wire or stimulating probe, such as the stimulating probe 401. The dilation system 400 includes a base 402, a first blade 404, a second blade 406, and an actuating mechanism 408 operably associated with the first blade 404 and the second blade 406 so as to cause the first blade 404 and the second blade 406 to move from a closed condition (FIG. 29) wherein the first blade 404 and the second blade 406 are positioned adjacent one another a distance to permit insertion through selected tissue to an expanded condition (FIGS. 30 and 31) wherein the first blade 404 and the second blade 406 are spread apart relative to one another a selected distance to expand the tissue.

The first blade 404 has a proximal end 410 and a distal end 412. The first blade 404 extends from the base 402 so that the distal end 412 of the first blade 404 extends away from the base 402 in such a way that the distal end 412 is deflectable relative to the proximal end 410. Similarly, the second blade 406 has a proximal end 414 and a distal end 416. The second blade 406 extends from the base 402 so that the distal end 416 of the second blade 406 extends away from the base 402 in such a way that the distal end 416 is deflectable relative to the proximal end 414. Each of the first blade 404 and the second blade 406 has a generally arcuate cross section and the distal ends 412 and 416 may be tapered to facilitate insertion into a patient. Each of the first blade 404 and the second blade 406 may be provided with a bore or channel (not shown) extending the length thereof for receiving an electrode (not shown) to aid in stimulating adjacent tissues.

Figure 32:
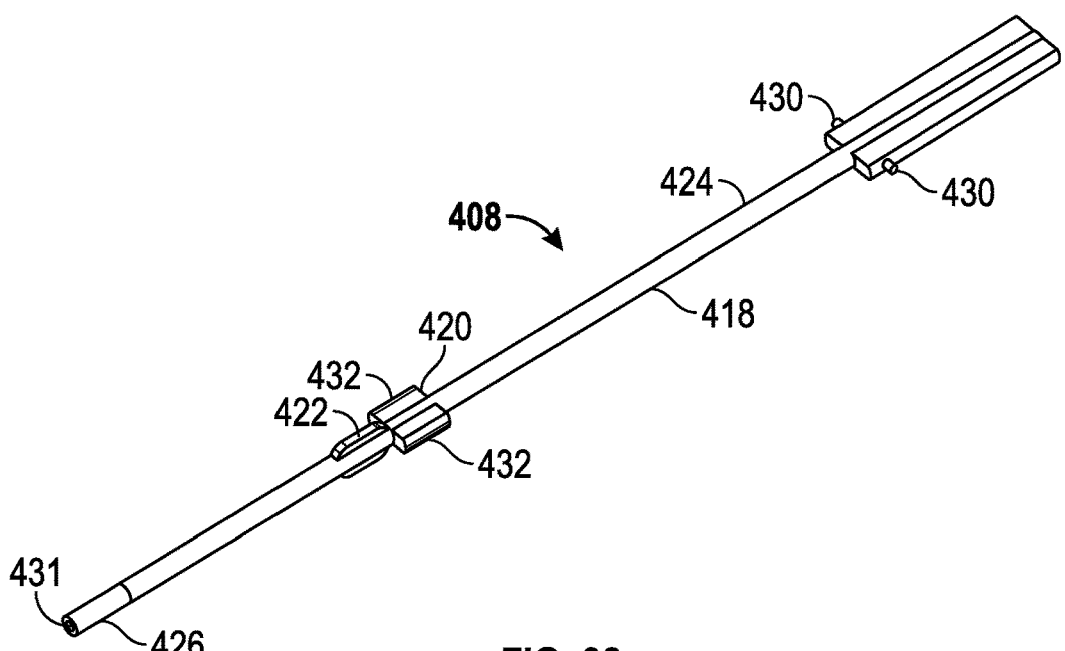
FIG. 32 is a perspective view of an expander.
Figure 33:
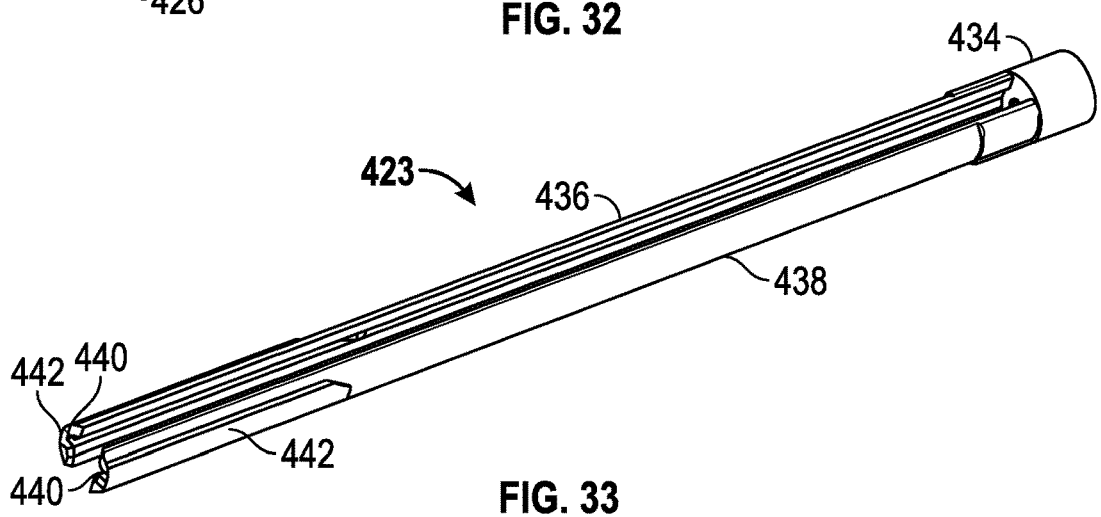
FIG. 33 is a perspective view of the secondary expander.

As best illustrated in FIGS. 32 and 33, the actuating mechanism 408 includes a drive rod 418, an expander member 420, a guide 422, and a second expander member 423 (FIG. 33). The drive rod 418 has a proximal end 424 and a distal end 426. The drive rod 418 extends between the first blade 404 and the second blade 406 and is rotatably connected to the base 402 in such a way that the drive rod 418 is rotatable through an angle of at least about 90 degrees. In one embodiment, the base 402 is provided with a pair of diametrically opposed slots 428 (only one slot 428 being visible), and the guide rod 418 is provided with a pair of diametrically opposed pins 430 extending radially therefrom and slidably received in the slots 428. The drive rod 418 has a central bore 431 sized to receive the stimulating probe 401.

The expander member 420 extends from the drive rod 418 in such a way that rotational movement of the drive rod 418 moves the first blade 404 and the second blade 406 from the closed condition to the expanded condition. As best illustrated in FIG. 32, the expander member 420 may include a pair of flanges or protrusions 432 that are sized and shaped to contact the first blade 404 and the second blade 406 and move the first blade 404 and the second blade 406 to the expanded condition upon rotation of the drive rod 418. The guide member 422 may extend from the drive rod 418 in a substantially perpendicular relationship of the expander member 420 for guiding the second expander member 423 in a manner to be discussed below.

The second expander member 423 is slidably positionable over the drive rod 418 and between the first blade 404 and the second blade 406 so as to extend between the first blade 404 and the second blade 406 to fill the gap between the longitudinal edges of the first blade 404 and the longitudinal edges of the second blade 406. The second expander 423 may include a base 434, a first blade 436 extending from the base 434, and a second blade 438 extending from the base 434 in a spaced apart, parallel relationship to the first blade 436 so that the first blade 436 and the second blade 438 are slidably positionable over the expander member 420 when the expander member 420 is rotated to the expanded condition. The first blade 436 and the second blade 438 may be provided with a slot 440 extending along at least a portion an inner surface thereof for slidingly receiving a portion of the guide member 422.

Each of the first blade 436 and the second blade 438 has a generally arcuate cross section and the distal ends may be provided with a raised area 442 which is positionable substantially flush with the outer surfaces of the first blade 404 and the second blade 406 in the expanded condition so that the first blade 436 and the second blade 438 cooperate with the first blade 404 and the second blade 406 to form a circular cross section of a selected diameter, e.g., 16 mm-22 mm.

As an alternative to use of the second expander 423 to fill the gaps between the first blade 404 and the second blade 406, it will be appreciated that the dilation system 400 may further include an expandable sheath positioned about at least the distal ends of the first blade 404 and the second blade 406 to cover the spaces between the first blade 404 and the second blade 406. As described above, the sheath can be made of any type of expandable material, such as a mesh, fabric, polymer, or elastomeric polymer.

Figure 34:
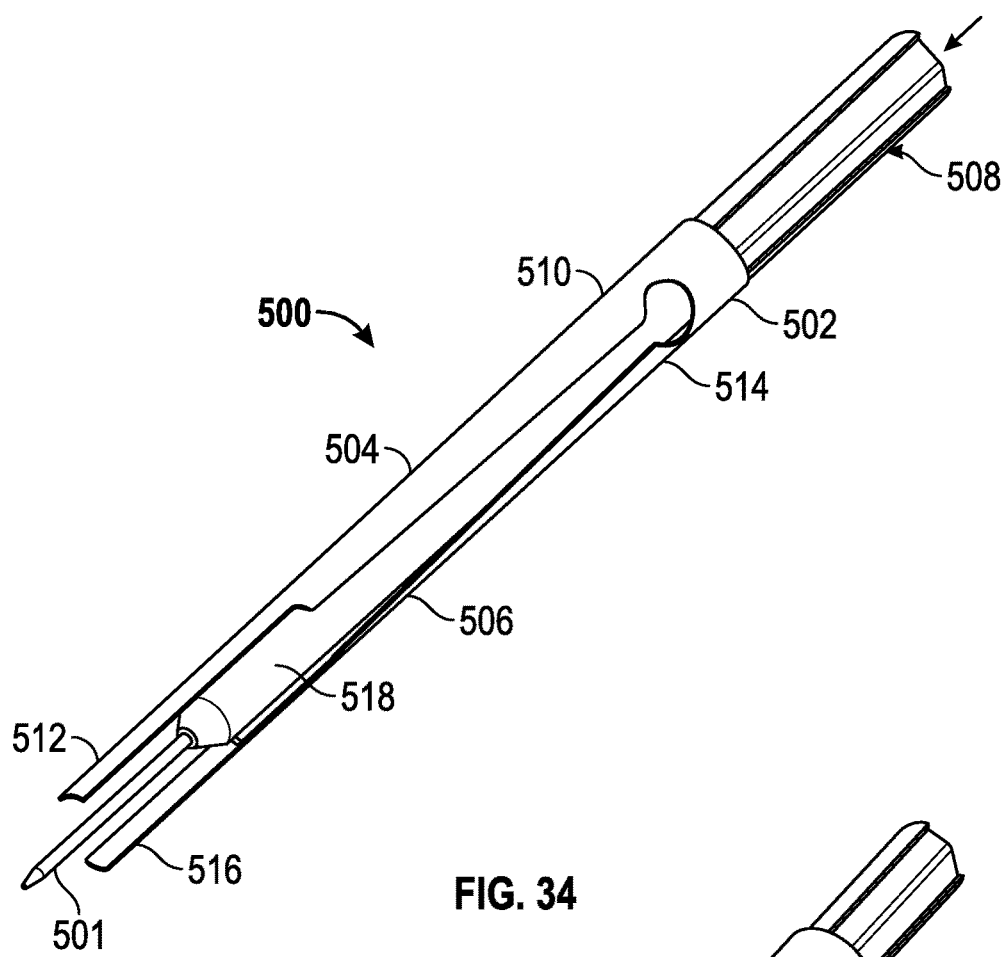
FIG. 34 is a perspective view of another embodiment of a dilation system constructed in accordance with the inventive concepts disclosed herein.
Figure 35:
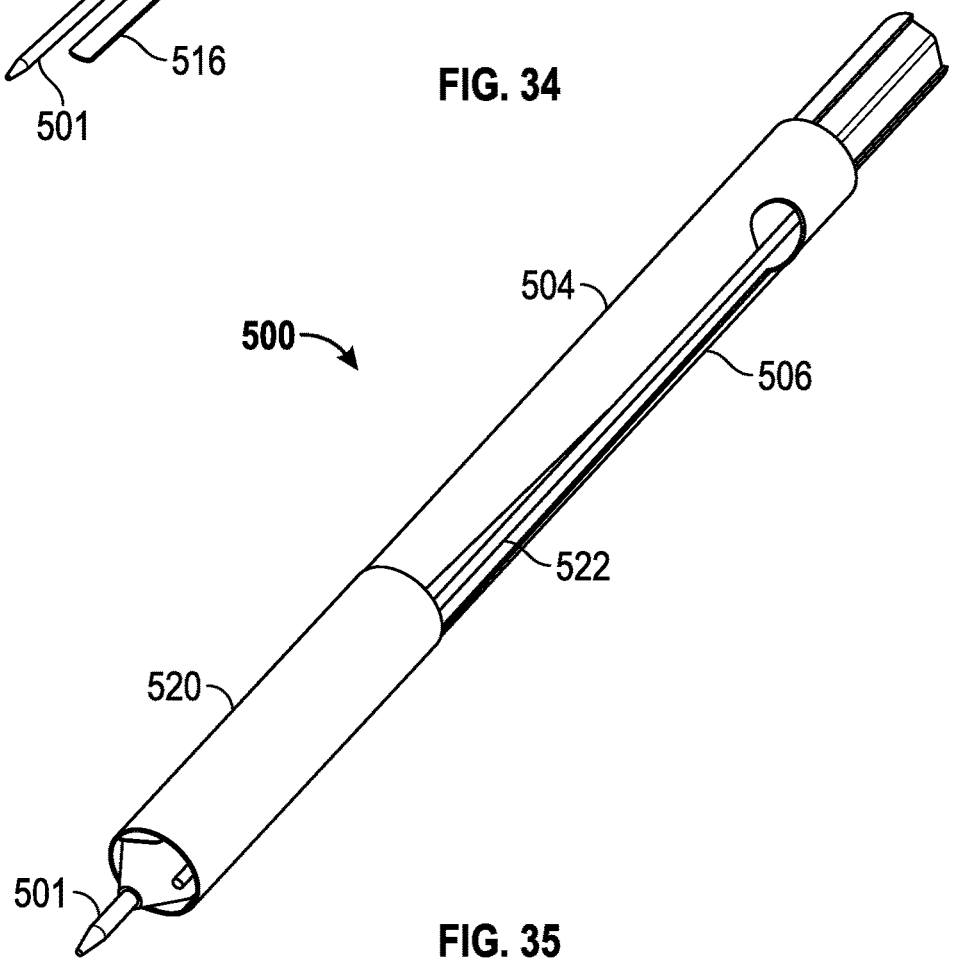
FIG. 35 is a perspective view of the dilation system of FIG. 34 shown provided with an expandable sheath.

FIGS. 34 and 35 illustrate another embodiment of a dilation system 500 constructed in accordance with the inventive concepts disclosed herein. The dilation system 500 is used to create an initial corridor which may be expanded to a desired diameter, e.g., 16-22 mm, without inserting any additional instruments. In addition, the dilation system 500 is adapted to be used with a k-wire or stimulating probe, such as a stimulating probe 501. The dilation system 500 includes a base 502, a first blade 504, a second blade 506, and an actuating mechanism 508 operably associated with the first blade 504 and the second blade 506 so as to cause the first blade 504 and the second blade 506 to move from a closed condition wherein the first blade 504 and the second blade 506 are positioned adjacent one another a distance to permit insertion through selected tissue to an expanded condition (FIGS. 34 and 35) wherein the first blade 504 and the second blade 506 are spread apart relative to one another a selected distance to expand the tissue.

The first blade 504 has a proximal end 510 and a distal end 512. The first blade 504 extends from the base 502 so that the distal end 512 of the first blade 504 extends away from the base 502 in such a way that the distal end 512 is deflectable relative to the proximal end 510. Similarly, the second blade 506 has a proximal end 514 and a distal end 516. The second blade 506 extends from the base 502 so that the distal end 516 of the second blade 506 extends away from the base 502 in such a way that the distal end 516 is deflectable relative to the proximal end 514. Each of the first blade 504 and the second blade 506 has a generally arcuate cross section and the distal ends 512 and 516 may be tapered to facilitate insertion into a patient. Each of the first blade 504 and the second blade 506 may be provided with a bore or channel (not shown) extending the length thereof for receiving an electrode (not shown) to aid in stimulating adjacent tissues.

The actuating mechanism 508 includes a drive rod 518 having a proximal end and a distal end. The drive rod is positioned between the first blade 504 and the second blade 506 and configured in such a way that axial movement of the drive rod 518 moves the first blade 504 and the second blade 506 from the closed condition to the expanded condition. The drive rod 518 may have a wedge shape so that axial movement of the drive rod 518 wedge will drive the first blade 504 and the second blade 506 in a radial direction to larger or smaller diameters.

The drive rod 518 may be moved in a variety of different ways. For example, the drive rod 518 may be axially moved manually by sliding the drive rod 518 between the first blade 504 and the second blade 506. Also, the drive rod 518 may be moved in a manner similar to that described above with respect to the dilation system 200 where the drive rod 518 may be moved with an internally threaded assembly, by way of example.

The expansion of the first blade 504 and the second blade 506 will leave gaps as they go to the large circumferences so these gaps should be covered to effectively dilate the tissue. To this end, the dilation system 500 may include an expandable sheath 520 (FIG. 35) positioned about at least the distal ends of the first blade 504 and the second blade 506 to cover the spaces between the first blade 504 and the second blade 506. The sheath 520 may be laterally supported by a plurality of support member 522 (only one support member 522 being visible in FIG. 35). As described above, the sheath 520 can be made of any type of expandable material, such as a mesh, fabric, polymer, or elastomeric polymer. The sheath 520 may alternatively be in the form of a plurality of metal slotted tubes connected to the blades 504 and 506. The slotted tubes must be made out of an elastic material such as nitinol to accommodate the bending to a larger diameter. The tubes are initially nested within each other. As the blades are driven radially outward they interact with each other such that the diameters of tubing will increase. The sliding and expanding action will maintain an enclosed cylinder with some discontinuities, but no gaps. Alternatively, the drive rod 518 may be configured to file in the gaps.

Referring now to FIGS. 36-38, another embodiment of a dilation system 600 is illustrated. The dilation system 600 includes a first dilator 601, an expandable dilator 602, and a plurality of expansion dilators 604 positionable between the first dilator 601 and the expandable dilator 602 to enlarge the surgical corridor and create an enlarged working space. The first dilator 601 is a generally tubular member with a bore 606 for receiving a K-wire or stimulating probe, such as the stimulating probe 118 of FIG. 14.

The expandable dilator 602 includes an expandable sheath 608 and a plurality of support members 610 extending longitudinally along an inner surface of the sheath 608 in a spaced apart relationship to provide longitudinal support to the sheath 608 while allowing for the sheath 608 to expand radially. The sheath 608 may be constructed of any suitable elastomeric material. The support members 610 are sized to extend along the length of the sheath 608 may be connected to sheath 602 in any suitable manner, such as use of an adhesive, weaving the support arms in the sheath 602, or embedding the support members 610 in the sheath 608, for example. While the expandable dilator 602 is shown as having four support members 608, it will be appreciated that the expandable dilator 602 may expand with the use of at least three support members 610. However, the sheath 608 will created a rounder corridor the more support members 610 that are utilized.

In use, the first dilator 601 is inserted through tissue up to a disc annulus while monitoring neural structures. A K-wire may be inserted through the bore 606 of the first dilator 601 to dock the first dilator 601 to a disc annulus. The expandable dilator 602 is then inserted over the first dilator 601 as shown in FIGS. 36A and 36B. A second dilator 604a (FIGS. 37A and 37B) may then be inserted between first dilator 601 and the expandable dilator 602, thereby expanding the sheath 608. As shown in FIGS. 38A and 38C, a third dilator 604b may be inserted between the second dilator 604a and the expandable dilator 602, thereby further expanding the sheath 608. A retractor (not shown) may be inserted about the sheath 608, and the dilation system 600 and the K-wire removed.

As shown, the support members 610 and the dilators 601, 604a and 604b may be provided with corresponding tongues 612 and grooves 614 for aligning the dilators to one another during expansion. The tongue and groove construction also allows the sheath 608 to expand uniformly. The dilation system 600 has an advantage in that only two dilators are inserted that pass through tissue which minimizes tissue trauma as the remaining dilators are used to expand the dilation system radially without any further insertion forces. This is due to the sheath remaining in contact with tissue for the remainder of the expansion.

Electrodes, such as electrode 616, may be embedded in or on the first dilator 601 and the sheath 608 to allow for surrounding neural tissue to be identified, monitored, and assessed based on distance and pathology.

Figure 39:
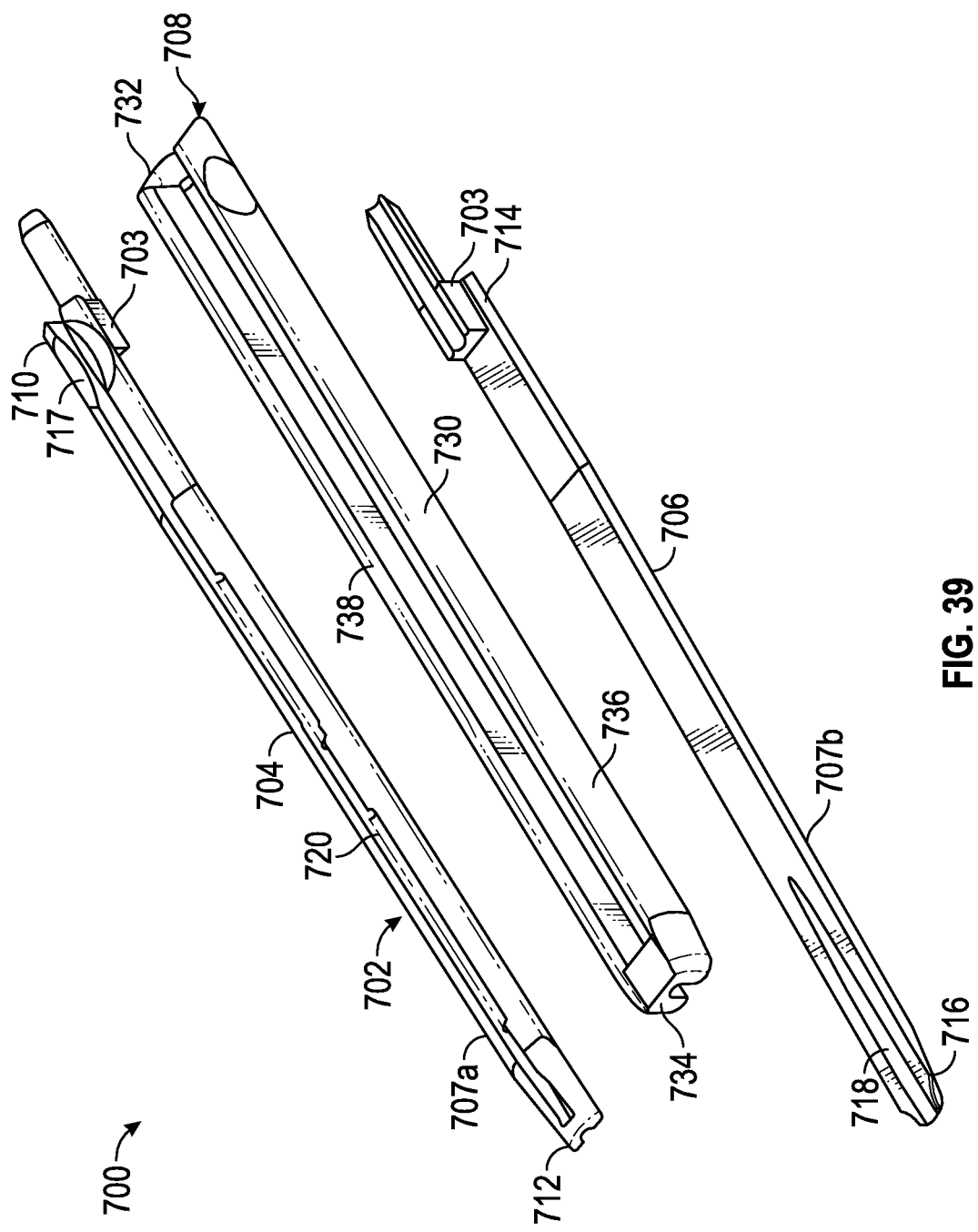
FIG. 39 is an exploded, perspective view of another embodiment of a dilation system constructed in accordance with the inventive concepts disclosed herein.

Referring now to FIGS. 39-41, another embodiment of a dilation system 700 is illustrated. The dilation system 700 is used to create an initial corridor which may be expanded to a desired diameter, e.g., 16-22 mm, without inserting any additional instruments. In addition, the dilation system 700 is adapted to be used with a k-wire or stimulating probe, such as the stimulating probe 701 (FIGS. 41A-41D). The dilation system 700 includes a wedge assembly 702 and an actuating assembly 708.

The wedge assembly 702 includes a base 703, a first blade 704, a second blade 706. The actuating mechanism 708 is operably associated with the first blade 704 and the second blade 706 so as to cause the first blade 704 and the second blade 706 to move from a closed condition (FIGS. 41A and 41B) wherein the distal ends of the first blade 704 and the second blade 706 are positioned adjacent one another to form a generally wedge shaped structure to facilitate insertion through selected tissue to an expanded condition (FIG. 41D) wherein the distal ends of the first blade 704 and the second blade 706 are spread apart relative to one another a selected distance to expand the tissue.

The base 703 serves to connect the first blade 704 to the second blade 706. The base 703 may include an elongated tubular portion 705 (best shown in FIG. 41D) for supporting and guiding the probe 701. As shown in FIG. 39, in one embodiment the wedge assembly 702 may be formed from two blade sections 707a and 707b to facilitate assembly with the actuating assembly 708. The blade sections 707a and 707b may be secured to one another at the base 703 in a suitable manner, such as with an adhesive or by welding, with the blades 704 and 706 straddling the actuating assembly 708.

The first blade 704 has a proximal end 710 and a distal end 712. The first blade 704 extends from the base 702 so that the distal end 712 of the first blade 704 extends away from the base 702 in such a way that the distal end 712 is deflectable relative to the proximal end 710. Similarly, the second blade 706 has a proximal end 714 and a distal end 716. The second blade 706 extends from the base 702 so that the distal end 716 of the second blade 706 extends away from the base 702 in such a way that the distal end 716 is deflectable relative to the proximal end 714. Each of the first blade 704 and the second blade 706 has a generally arcuate cross section and the distal ends 712 and 716 may be tapered to facilitate insertion into a patient. To assist in insertion of the wedge assembly 702 to be described below, each of the first blade 704 and the second blade 706 may be provided with a finger indention 717 near the proximal ends thereof.

Each of the first blade 704 and the second blade 706 may be provided with a channel 718 (FIG. 39) on an inner surface thereof extending to the distal end sized to receive the stimulating probe 701 when the first blade 704 and the second blade 706 are in the closed condition. At least one of the first blade 704 and the second blade 706 may also be provided with a longitudinal slot or channel 720 (FIG. 39) along a portion of an outer surface thereof for receiving a second stimulating probe 722 (FIG. 41B) when the first blade 704 and the second blade 706 are in the closed condition. The slot 720 may include one or more tabs 721 (FIG. 41A) extending inwardly into the slot 722 for gripping the probe 722 when the probe 720 is positioned in the slot 720.

The actuating mechanism 708 includes a drive member 730 positioned between the first blade 704 and the second blade 706 and configured in such a way that axial movement of the drive member 730 moves the first blade 704 and the second blade 706 from the closed condition to the expanded condition and causes the drive member 730 to extend between the first blade 704 and the second blade 706 to fill the gap between the longitudinal edges of the first blade 704 and the longitudinal edges of the second blade 706.

The drive member 730 has a proximal base 732, a distal base 734, a first blade 736 extending between the proximal base 732 and the distal base 734, a second blade 738 extending between the proximal base 732 and the distal base 734 in a spaced apart, parallel relationship to the first blade 736 so that the first blade 736 and the second blade 738 are slidably positionable between the first blade 704 and the second blade 706. To assist in insertion of the drive member 730 in a manner to be described below, each of the first blade 736 and the second blade 738 may be provided with a finger indention 739 near the proximal ends thereof.

Figure 41A:
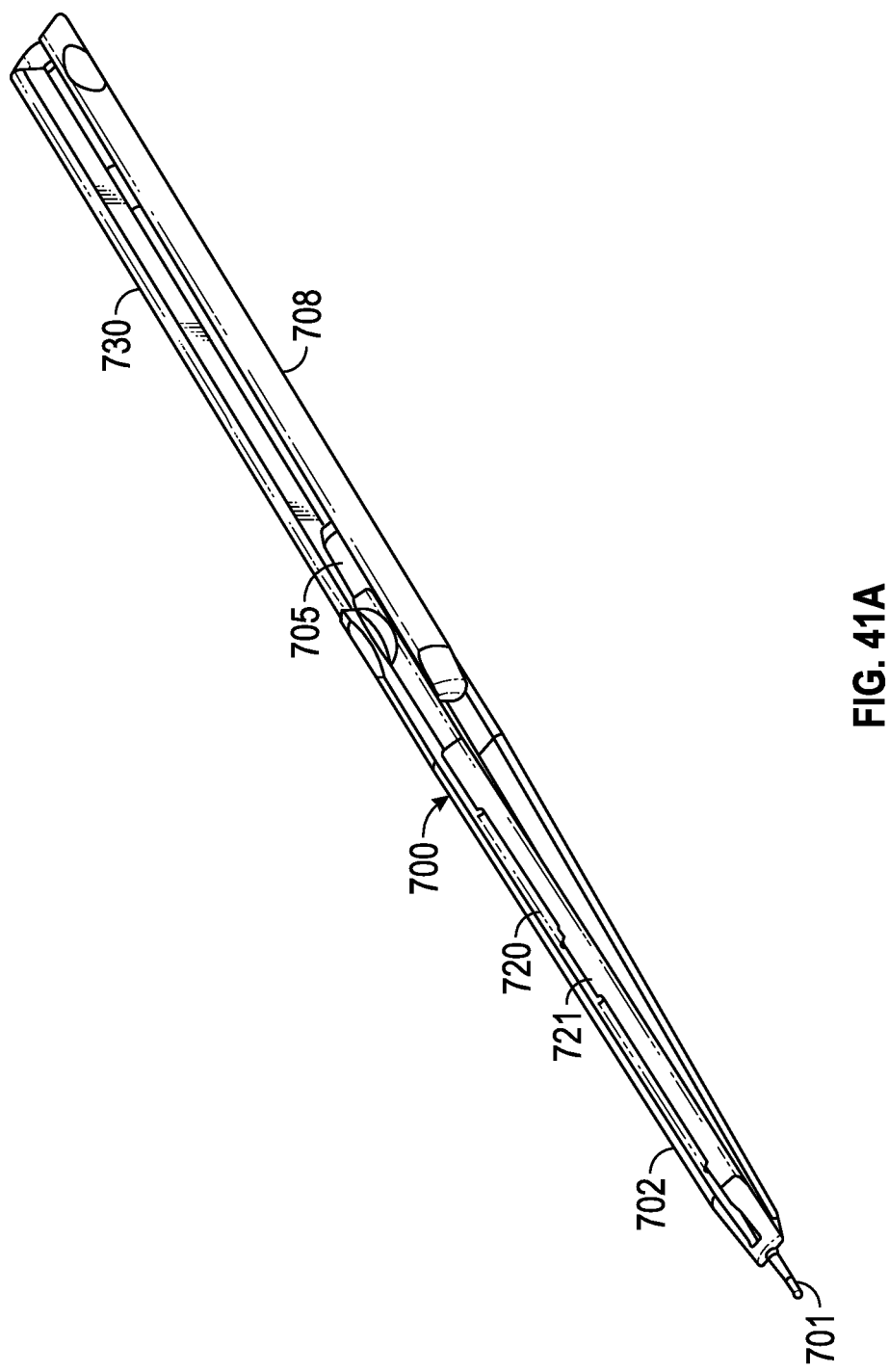
FIG. 41A is a perspective view of the dilator system of FIG. 39 shown in a closed condition with a stimulating probed positioned therein.
Figure 41B:
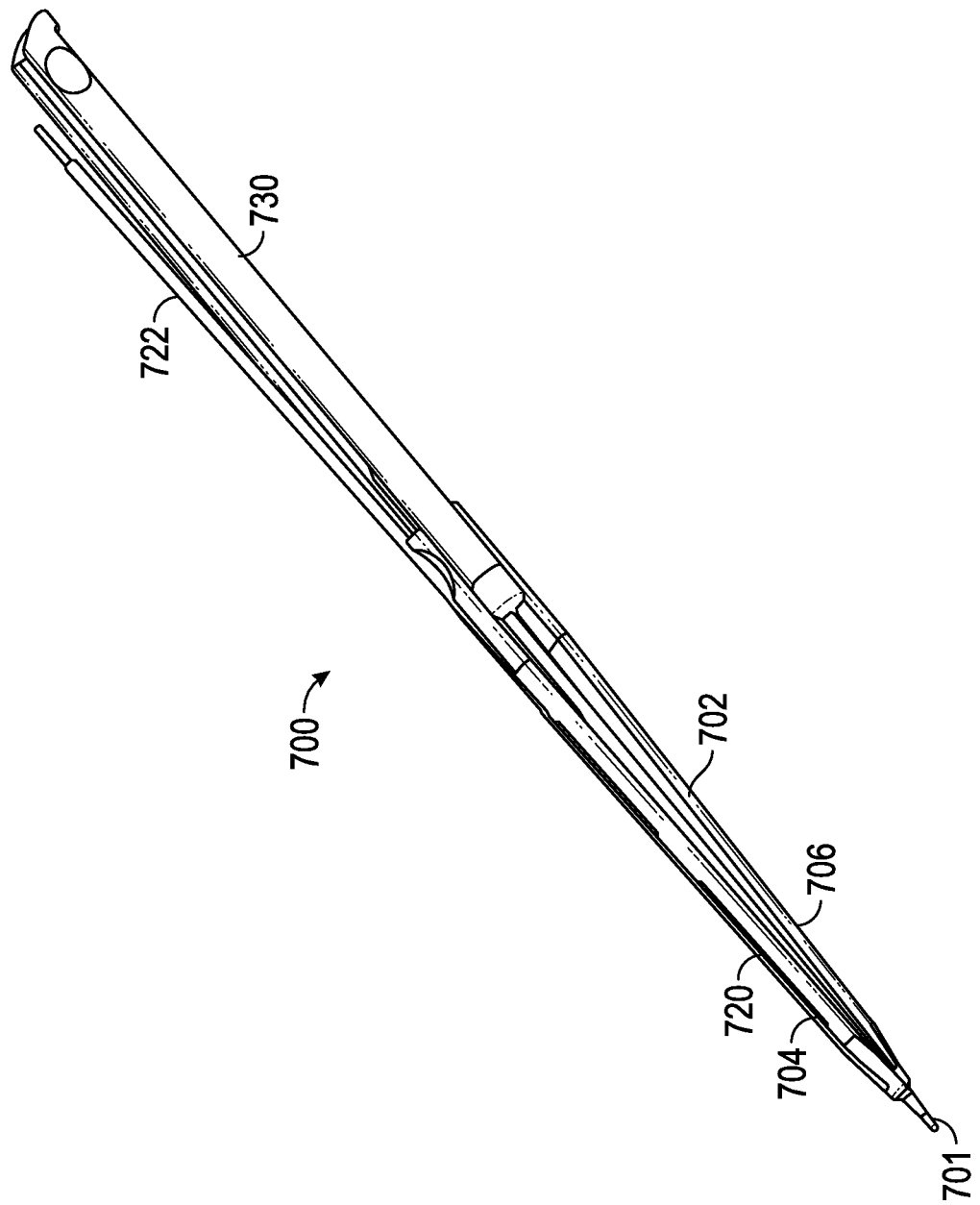
FIG. 41B is a perspective view of the dilator system of FIG. 39 shown in a closed condition with a second stimulating probed positioned therein.
Figure 41C:
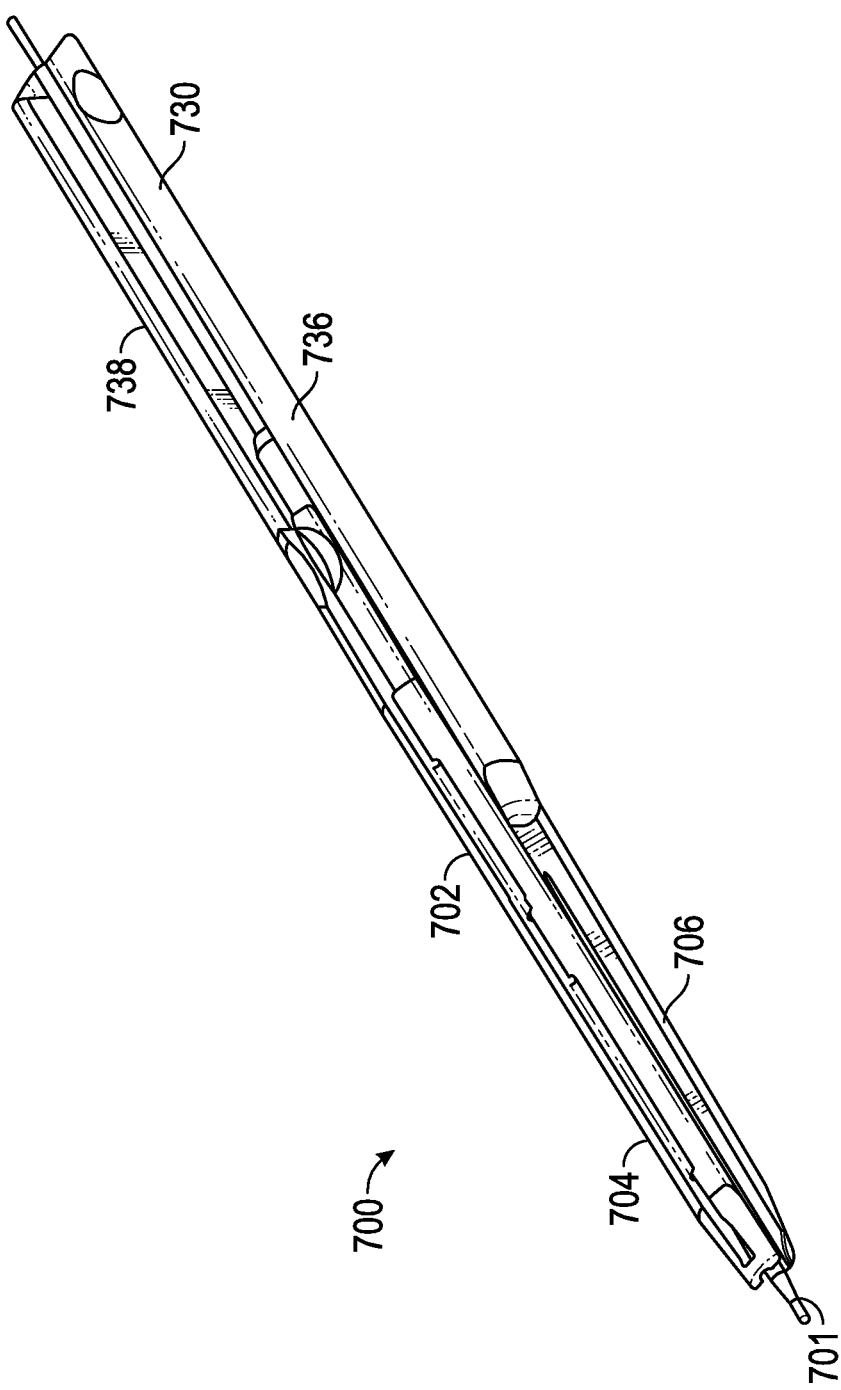
FIG. 41C is a perspective view of the dilator system of FIG. 39 shown in a partially expanded condition.
Figure 41D:
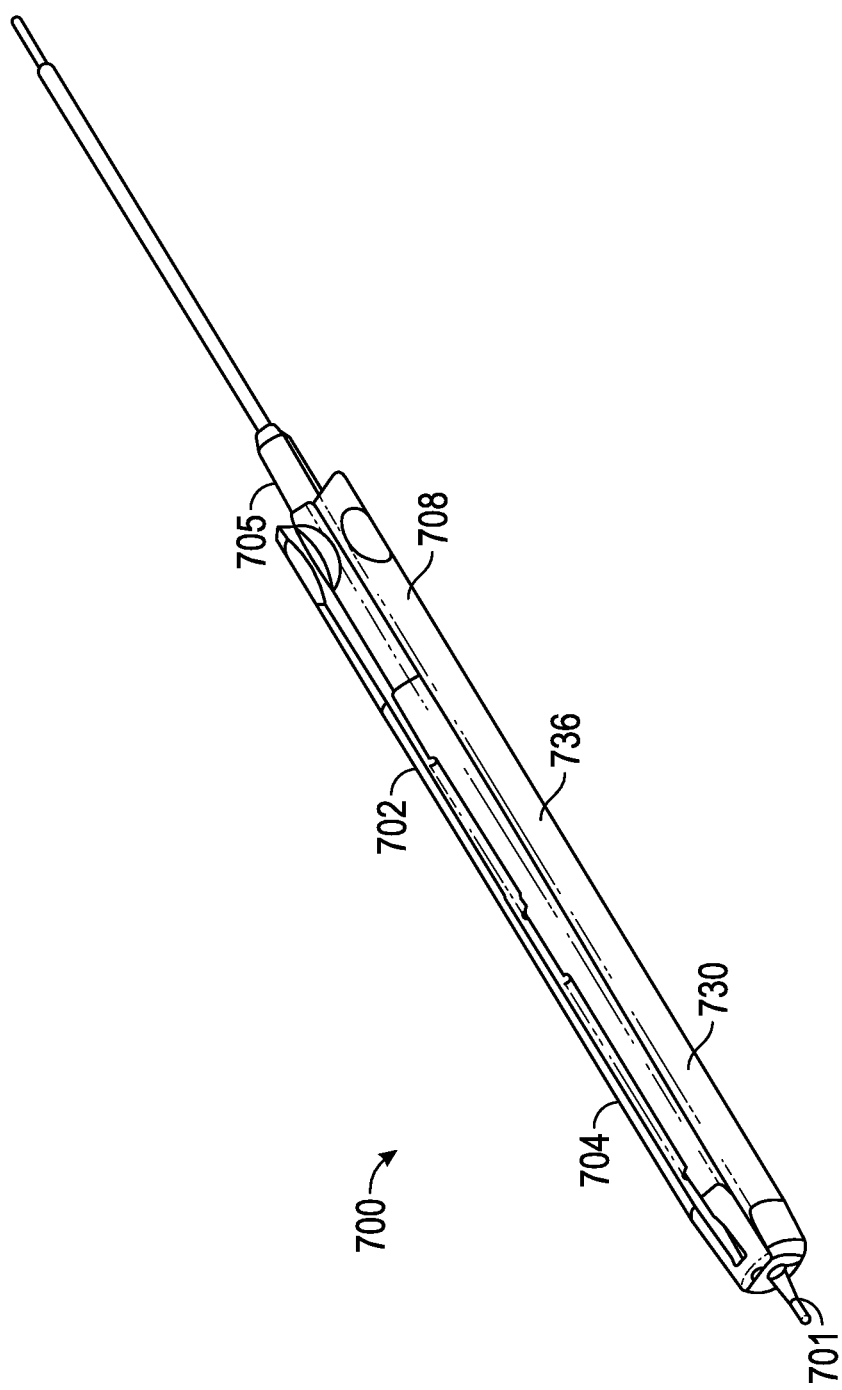
FIG. 41D is a perspective view of the dilator system of FIG. 39 shown in an expanded condition.

The longitudinal edges of the first blade 736 and the second blade 738 are configured to mate with the longitudinal edges of the first blade 704 and the second blade 706 so that the outer surfaces of the first blade 736 and the second blade 738 are substantially flush with the outer surfaces of the first blade 704 and the second blade 706 in the expanded condition (FIG. 41D). As a result, the wedge assembly 702 and the drive member 730 cooperate to form a circular cross section of a selected diameter, e.g., 16-22 mm, about which a retractor assembly (not shown) may be disposed.

The proximal base 732 of the drive member 730 serves to connect the proximal ends of the first blade 736 and the second blade 738 to one another. In one embodiment, the proximal base 732 is generally U-shape to provide an open side which facilitates insertion of the probe 722 into the slot 720. The proximal base 732 is configured to receive the tubular portion 705 of the base 703 and to contact the proximal end of one of the first and second blades 704 and 706 in way that the contact between the proximal base 730 and wedge assembly 702 serve to limit the movement of the actuating assembly 708 relative to the wedge assembly 702.

Figure 40A:
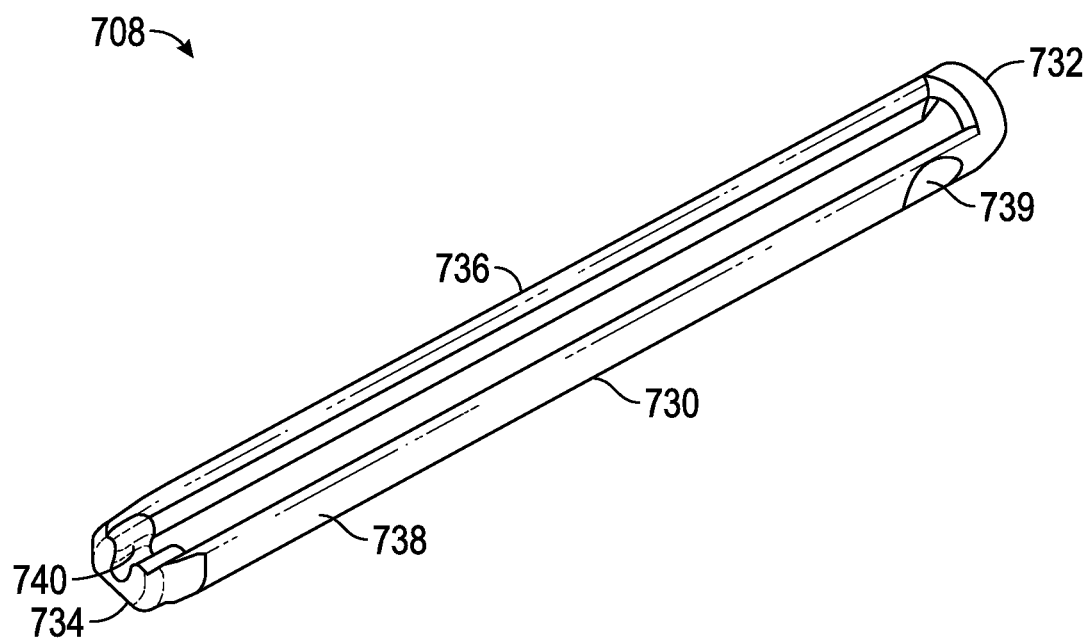
FIG. 40A is perspective view of a drive member.
Figure 40B:
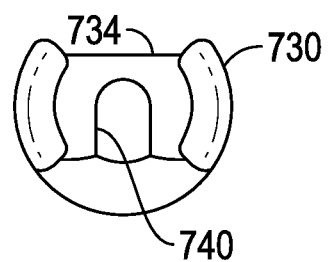
FIG. 40B is a distal end view of the drive member of FIG. 40A.

Referring to FIGS. 40A and 40B, the distal base 734 is configured to slidingly mate with the inner surface of the first and second blades 704 and 706 to cause the first and second blades 704 and 706 to move from the closed condition to the expanded condition when the distal base 734 is caused to be axially moved from the proximal ends of the first and second blades 704 and 706 to the distal ends of the first and second blades 704 and 706. The distal base 734 is provided with an open sided hole 740 for supporting and guiding the probe 701.

In use, the probe 701 is initially positioned through the psoas to the designated disc space to define a central location for subsequent instrumentation. Following positioning of the probe 701, the dilator system 700 is inserted over the probe 701 with the dilator system 700 in the closed position (FIG. 41A) by pushing the wedge assembly 702 axially along the probe 701. With the wedge assembly 702 in the closed condition, the psoas is enlarged to an approximate oval shape. As illustrated in FIG. 41B, the slot 720 in the outer surface of one of the first and second blades 704 and 706 allows the second probe 722 to be used during the insertion process. The probe 722 can be manipulated, and the dilator system 700 rotated to assist with neural monitoring.

After the wedge assembly 702 has been positioned up to the disc space, the drive member 730 is pushed axially toward the distal ends of the first and second blades 704 and 706 in manner to move the first blade 704 and the second blade 706 from the closed condition to the expanded condition (FIG. 41D) and cause the drive member 730 to extend between the first blade 704 and the second blade 706 to fill the gap between the longitudinal edges of the first blade 704 and the longitudinal edges of the second blade 706 (FIG. 41D). When the drive member 730 is moved to the disc space, the outer surfaces of the first blade 736 and the second blade 738 are substantially flush with the outer surfaces of the first blade 704 and the second blade 706 in the expanded condition (FIG. 41D) and thereby cooperate to form a circular cross section of a selected diameter about which a retractor assembly (not shown) may be disposed.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. A method of forming an access opening through a psoas muscle to a patient's spine, comprising the steps of:
    laterally inserting a stimulating probe into the psoas muscle;
    transmitting an electrical pulse via an electromyograph (EMG) into the stimulating probe to locate a safe zone in the psoas muscle;
    laterally inserting the stimulating probe through the psoas muscle so a probe tip is proximate the patients spine;
    inserting a wedge assembly through the psoas muscle and toward the patients spine guided by sliding engagement of the stimulating probe; and
    expanding the wedge assembly from a dosed condition to an expanded condition,
    wherein the wedge assembly comprises at least a first blade and a second blade with each of the first blade and the second blade having a proximal end, a distal end, and an arcuate outer surface,
    wherein when the wedge assembly is in the closed condition, the arcuate outer surface of the first blade and the arcuate outer surface of the second blade are in a tapering relationship relative one another from the proximal end of the first blade and the second blade to the distal end of the first blade and the second blade, and
    wherein the step of expanding the wedge assembly further comprises the step of moving the distal ends of the first blade and the second blade in a radially outward direction relative to one another so the first blade and the second blade are in a substantially parallel relationship relative to one another.

2. The method of claim 1, further comprising:
    inserting a second stimulating probe along the outer surface of the wedge assembly; and
    transmitting an electrical pulse via the EMG into the second stimulating probe to locate a safe zone in the psoas muscle.

3. The method of claim 1, wherein in the step of moving the distal end of the blades of the wedge assembly further includes axially moving a drive member positioned between the first blade and the second blade in a way that moves the first blade and the second blade from the closed condition to the expanded condition.

4. The method of claim 3, wherein the drive member includes a plurality of parallel blades, and wherein the step of moving the distal end of the blades of the wedge assembly further comprises positioning the blades of the drive member between the blades of the wedge assembly to fill a space between the blades of the wedge assembly as the blades of the wedge assembly are moved from the closed condition to the expanded condition.

5. The method of claim 1, further comprising positioning an expandable sheath about at least the distal ends of the first blade and the second blade.

6. A method of forming an access opening through a psoas muscle to a patient's spine, comprising the steps of:
    laterally inserting a stimulating probe into the psoas muscle;
    transmitting an electrical pulse via an electromyograph (EMG) into the stimulating probe to locate a safe zone in the psoas muscle;
    laterally inserting the stimulating probe through the psoas muscle so a probe tip is proximate the patients spine;
    inserting a wedge assembly through the psoas muscle and toward the patient's spine guided by sliding engagement of the stimulating probe; and
    expanding the wedge assembly from a closed condition to an expanded condition,
    wherein the wedge assembly comprises at least a first blade and a second blade with each of the first blade and the second blade having a proximal end and a distal end, and wherein the step of expanding the wedge assembly further comprises the step of moving the distal ends of the first blade and the second blade in a radially outward direction relative to one another so the first blade and the second blade are in a substantially parallel relationship relative to one another,
    wherein each of the first blade and the second blade has an arcuate outer surface and an inner surface, and wherein in the step of expanding the wedge member from the closed condition to the expanded condition, the arcuate outer surfaces of the blades are in a tapering relationship relative one another from the proximal end of the first blade and the second blade to the distal end of the first blade and the second blade so the arcuate outer surfaces of the first blade and the second blade cooperate with one another to form an oblong transverse profile in the closed condition, and the distal ends of the first blade and the second blade are spread apart relative to the position of the distal ends of the first blade and the second blade when in the closed condition so the arcuate outer surfaces of the first blade and the second blade cooperate with one another to form a substantially circular transverse profile in the expanded condition.

7. A method of forming an access opening through a psoas muscle to a patient's spine, comprising the steps of:
laterally inserting a stimulating probe into the psoas muscle;
transmitting an electrical pulse via an electromyograph (EMG) into the stimulating probe to locate a safe zone in the psoas muscle;
laterally inserting the stimulating probe through the psoas muscle so a probe tip is proximate the patients spine;
inserting a wedge assembly through the psoas muscle and toward the patient's spine guided by sliding engagement of the stimulating probe; and
expanding the wedge assembly from a dosed condition to an expanded condition,
wherein the wedge assembly comprises at least a first blade and a second blade with each of the first blade and the second blade having a proximal end and a distal end, and wherein the step of expanding the wedge assembly further comprises the step of moving the distal ends of the first blade and the second blade in a radially outward direction relative to one another so the first blade and the second blade are in a substantially parallel relationship relative to one another,
wherein in the step of moving the distal end of the blades of the wedge assembly further includes axially moving a drive member positioned between the first blade and the second blade in a way that moves the first blade and the second blade from the closed condition to the expanded condition,
wherein the drive member includes a plurality of parallel blades, and wherein the step of moving the distal end of the blades of the wedge assembly further comprises positioning the blades of the drive member between the blades of the wedge assembly to fill a space between the blades of the wedge assembly as the blades of the wedge assembly are moved from the closed condition to the expanded condition,
wherein the drive member has a proximal base, a distal base, a first blade extending between the proximal base and the distal base and having an outer surface, a second blade extending between the proximal base and the distal base in a spaced apart, parallel relationship to the first blade and having an outer surface, and wherein in the step of positioning the first blade and the second blade of the drive member further comprises slidably positioning the first blade and the second blade of the drive member between the first blade and the second blade of the wedge assembly.

8. The method of claim 7, wherein the first blade of the drive member has longitudinal edges extending from the proximal base to the distal base, wherein the second blade of the drive member has longitudinal edges extending from the proximal base to the distal base, wherein the first blade of the wedge assembly has longitudinal edges, wherein the second blade of the wedge assembly has longitudinal edges, and wherein in the step of positioning the blades of the drive member further comprises mating the longitudinal edges of the first blade and the second blade of the drive member with the longitudinal edges of the first blade and the second blade of the wedge assembly so the outer surfaces of the first blade and the second blade of the drive member are flush with the arcuate outer surfaces of the first blade and the second blade of the wedge assembly in the expanded condition.

9. The method of claim 7, wherein the distal base of the drive member is slidingly mated with the inner surfaces of the first blade and the second blade of the wedge assembly, and wherein in the step of positioning the the first blade and the second blade of the drive member further comprises axially moving the distal base from the proximal ends of the first blade and the second blade of the wedge assembly to the the distal ends of the first blade and the second blade of the wedge assembly to cause the first blade and the second blade of the wedge assembly to move from the closed condition to the expanded condition.

* * * * *